US007498492B2

(12) United States Patent
Ruan et al.

(10) Patent No.: US 7,498,492 B2
(45) Date of Patent: Mar. 3, 2009

(54) MODIFICATION OF SUCROSE SYNTHASE GENE EXPRESSION IN PLANT TISSUE AND USES THEREFOR

(75) Inventors: Yong-Ling Ruan, Nicholls (AU); Robert Furbank, Weetangara (AU); Danny Llewellyn, O'Connor (AU)

(73) Assignee: Commonwealth Scientific and Industrial Research Organization, Campbell (AU)

( * ) Notice: Subject to any disclaimer, the term of this patent is extended or adjusted under 35 U.S.C. 154(b) by 526 days.

(21) Appl. No.: 10/003,405

(22) Filed: Dec. 6, 2001

(65) Prior Publication Data

US 2002/0116736 A1    Aug. 22, 2002

Related U.S. Application Data

(60) Provisional application No. 60/251,852, filed on Dec. 8, 2000.

(51) Int. Cl.
*C12N 15/29* (2006.01)
*C12N 15/52* (2006.01)
*C12N 15/82* (2006.01)
*A01H 5/00* (2006.01)
*A01H 5/10* (2006.01)

(52) U.S. Cl. .................. 800/314; 800/284; 800/287; 800/290; 800/298

(58) Field of Classification Search ................ 800/278, 800/284, 287, 298, 314; 536/23.1, 23.2, 536/23.6
See application file for complete search history.

(56) References Cited

U.S. PATENT DOCUMENTS 6,080,914 A * 6/2000 Conner ....................... 800/298
6,268,546 B1 * 7/2001 McBride et al. ............. 800/282

OTHER PUBLICATIONS

Barratt D. et al. Plant Physiology, Oct. 2001 vol. 127; pp. 655-664.*
Chourey P. et al. Mol. Gen. Genet. 1998, vol. 259, pp. 88-96.*
Ruan Y. et al. Plant Physiology, vol. 115, pp. 375-385.*
GenBank Accession No. L19762 (GI: 349737)—"Lycopersicon esculentum fruit sucrose synthase mRNA, complete cds;" Jun. 20, 1994.
GenBank Accession No. X69931 (GI: 19099)—"H. vulgare mRNA for sucrose synthase;" May 11, 1995.
GenBank Accession No. Z15028.1 (GI: 20373)—"O.sativa mRNA for sucrose synthase;" Oct. 12, 1992.
GenBank Accession No. Z11532.1 (GI: 21341)—"S.officianarum SUS1 mRNA for sucrose synthase;" Feb. 9, 1999.
GenBank Accession No. M18745.1 (GI: 169571)—"Potato sucrose synthase mRNA, complete cds;" Apr. 27, 1993.
GenBank Accession No. L22296 (GI: 51945)—"Zea mays sucrose synthase (Sus1) mRNA, complete cds;" Jul. 22, 1994.
GenBank Accession No. U73588 (GI: 4733945)—"Gossypium hirsutum sucrose synthase mRNA, complete cds;" May 4, 1999.
GenBank Accession No. X81974 (GI: 1488569)—"B.vulgaris mRNA for sucrose synthase;" Mar. 25, 1997.
GenBank Accession No. X75332 (GI: 406316)—"D.carota (Nantaise) mRNA for sucrose synthase;" Sep. 9, 2004.
GenBank Accession No. X69773.1 (GI: 22037)—"V.faba mRNA for sucrose synthase;" May 11, 1995.
Y. Amor et al., "A Membrane-Associated Form of Sucrose Synthase and Its Potential Role in Synthesis of Cellulose and Callose in Plants", *Proc. Nat'l. Acad. Sci. USA*, vol. 92, pp. 9353-9357, Sep. 1995.
Y. Ruan et al, "The Differential Expression of Sucrose Synthase in Relation to Diverse Patterns of Carbon Partitioning in Developing Cotton Seed", *Plant Physiol.* (1997) vol. 115, pp. 375-385.
Y. Ruan et al, "A Fiberless Seed Mutation in Cotton is Associated with Lack of Fiber Cell Initiation in Ovule Epidermia and Alterations in Sucrose Synthase-Expression and Carbon Partitioning in Developing Seeds", *Plant Physiol.* (1998) vol. 118, pp. 399-406.
Y. Ruan et al, "Pathway and Control of Sucrose Import Into Initiating Cotton Fibre Cells", *Aust. J. Plant Physiol.*, (2000) vol. 27, pp. 795-800.
Sumant Chengappa et al, "Transgenic Tomato Plants With Decreased Sucrose Synthase are Unaltered in Starch and Sugar Accumulation in the Fruit", *Plant Molecular Biology* vol. 40, pp. 213-221 (1999).
Yong-Ling Ruan et al., "The Differential Expression of Sucrose Synthase in Relation to Diverse Patterns of Carbon Partitioning in Cotton Seed", *Plant Physiol.* vol. 115, pp. 375-385 (1997).
Yong-Ling Ruan et al., "A Fiberless Seed Mutation in Cotton is Associated with Lack of Fiber Cell Initiation in Ovule Epidermis and Alterations in Sucrose Synthase-Expression and Carbon Partitioning in Developing Seeds", *Plant Physiol.*, vol. 118, pp. 399-406 (1998).
Marc-Andre D'Aoust et al., "Antisense Inhibition of Tomato Fruit Sucrose Synthase Decreases Fruit Setting and the Sucrose Unloading Capacity of Young Fruit", *The Plant Cell*, vol. 11, pp. 2407-2418 (1999).
Candace H. Haigler et al., "Carbon Partitioning to Cellulose Synthesis" *Plant Molecular Biology*, vol. 47, pp. 29-51 (2001).
Yong-Ling Ruan et al., "Pathway and Control of Sucrose Import Into Initiating Cotton Fibre Cells", *Aust. J. Plant Physiol.* vol. 27, pp. 297-800 (2000).
Yoshinori Shimizu et al, "Changes in Levels of mRNAs for Cell Wall-Related Enzyme sin Growing Cotton Fiber Cells", *Plant Cell Physiol.* vol. 38(3), pp. 375-378 (1997).
Tang, Guo-Qing et al., "Antisense repression of sucrose synthase in carrot (*Daucus carota* L.) affects growth rather than sucrose partitioning." *Plant Molecular Biology*, 41, 1999, Kluwer Academic Publishers, pp. 465-479.

* cited by examiner

*Primary Examiner*—Russell Kallis
(74) *Attorney, Agent, or Firm*—Buchanan Ingersoll & Rooney PC

(57) ABSTRACT

Methods and means are provided to modulate fiber quality in fiber-producing plants, such as cotton by modulating sucrose synthase activity and/or expression in such plants. The methods and means may also be used to obtain plants with seedless fruits or male-sterile plants.

11 Claims, 9 Drawing Sheets

B. Line 147# 2

A. WT

SEQUENCE LISTING

```
<160> NUMBER OF SEQ ID NOS: 6

<210> SEQ ID NO 1
<211> LENGTH: 2625
<212> TYPE: DNA
<213> ORGANISM: Gossypium hirsutum
<220> FEATURE:
<221> NAME/KEY: misc_feature
<222> LOCATION: (1240)..(1240)
<223> OTHER INFORMATION: n = any nucleotide (a,g,c,t)
<221> NAME/KEY: CDS
<222> LOCATION: (1)..(2625)
<223> OTHER INFORMATION:

<400> SEQUENCE: 1 atg gct gag cgt gct ctc act cgc gtc cac agt ctc cgt gag cgt ttg        48
Met Ala Glu Arg Ala Leu Thr Arg Val His Ser Leu Arg Glu Arg Leu
1               5                   10                  15 gat gag acc ctt ctt gct cac agg aac gag att ttg gcc ttg ctc tca        96
Asp Glu Thr Leu Leu Ala His Arg Asn Glu Ile Leu Ala Leu Leu Ser
            20                  25                  30 agg atc gag ggc aaa gga aaa gga att ctg caa cac cat caa att att       144
Arg Ile Glu Gly Lys Gly Lys Gly Ile Leu Gln His His Gln Ile Ile
        35                  40                  45 cta gag ttt gaa gct atc cct gaa gag aac aga aag aag ctc gct aat       192
Leu Glu Phe Glu Ala Ile Pro Glu Glu Asn Arg Lys Lys Leu Ala Asn
    50                  55                  60 ggt gca ttt ttt gaa gta ttg aag gct agt cag gaa gcg atc gtg ttg       240
Gly Ala Phe Phe Glu Val Leu Lys Ala Ser Gln Glu Ala Ile Val Leu
65                  70                  75                  80 cct cca tgg gtt gca ctt gct gtt cgt cca agg cct ggt gtt tgg gag       288
Pro Pro Trp Val Ala Leu Ala Val Arg Pro Arg Pro Gly Val Trp Glu
```

-continued

| | | | | | | | | | | | | | | | | |
|---|---|---|---|---|---|---|---|---|---|---|---|---|---|---|---|---|
| | | 85 | | | | 90 | | | | | 95 | | | | | |

```
tac att aga gtg aat gtt cac gcc ctt gtt gtt gag gaa ctc act gtt        336
Tyr Ile Arg Val Asn Val His Ala Leu Val Val Glu Glu Leu Thr Val
            100                 105                 110 gct gag tat ctc cac ttc aag gaa gag ctt gtt gat gga agt tca aat        384
Ala Glu Tyr Leu His Phe Lys Glu Glu Leu Val Asp Gly Ser Ser Asn
        115                 120                 125 gga aac ttt gtt ttg gaa ttg gat ttt gag ccc ttc aac tca tca ttc        432
Gly Asn Phe Val Leu Glu Leu Asp Phe Glu Pro Phe Asn Ser Ser Phe
    130                 135                 140 ccc cgc cca act ctt tca aaa tcc att ggt aat ggt gtg gag ttc cta        480
Pro Arg Pro Thr Leu Ser Lys Ser Ile Gly Asn Gly Val Glu Phe Leu
145                 150                 155                 160 aat cgt cac ctt tcg gca aaa ttg ttc cat gac aag gag agc atg cac        528
Asn Arg His Leu Ser Ala Lys Leu Phe His Asp Lys Glu Ser Met His
                165                 170                 175 cct ttg ctc gaa ttc ctc aga gtc cat tgt cac aag ggc aag aac atg        576
Pro Leu Leu Glu Phe Leu Arg Val His Cys His Lys Gly Lys Asn Met
            180                 185                 190 atg ttg aat gac aga att cag aac ttg aat gct ctt caa cat gtt ttg        624
Met Leu Asn Asp Arg Ile Gln Asn Leu Asn Ala Leu Gln His Val Leu
        195                 200                 205 agg aaa gca gag gag tat ctt ggt acc cta cct cct gag aca cca tgt        672
Arg Lys Ala Glu Glu Tyr Leu Gly Thr Leu Pro Pro Glu Thr Pro Cys
    210                 215                 220 gcc gaa ttc gaa cac cgg ttc cag gaa atc ggt ttg gaa aga ggt tgg        720
Ala Glu Phe Glu His Arg Phe Gln Glu Ile Gly Leu Glu Arg Gly Trp
225                 230                 235                 240 ggt gac acc gca gaa cgc gtg ctc gag atg atc caa ctc ctt ttg gat        768
Gly Asp Thr Ala Glu Arg Val Leu Glu Met Ile Gln Leu Leu Leu Asp
                245                 250                 255 ctt ctt gag gca act gat cct tgc acc ctt gag aag ttc ctt ggg aga        816
Leu Leu Glu Ala Thr Asp Pro Cys Thr Leu Glu Lys Phe Leu Gly Arg
            260                 265                 270 atc ccc atg gtg ttc aat gtt gtg att ctc act ccc cac gga tac ttc        864
Ile Pro Met Val Phe Asn Val Val Ile Leu Thr Pro His Gly Tyr Phe
        275                 280                 285 gct caa gac aat gtt ttg ggg tat ccc gac acc ggt ggg cag gtt gtt        912
Ala Gln Asp Asn Val Leu Gly Tyr Pro Asp Thr Gly Gly Gln Val Val
    290                 295                 300 tac atc ttg gat caa gtc cga gct ttg gag aat gag atg ctc ctc cgt        960
Tyr Ile Leu Asp Gln Val Arg Ala Leu Glu Asn Glu Met Leu Leu Arg
305                 310                 315                 320 ata aag caa caa gga ctc aac atc acc cct cga atc ctc att att act        1008
Ile Lys Gln Gln Gly Leu Asn Ile Thr Pro Arg Ile Leu Ile Ile Thr
                325                 330                 335 aga ctt ctt cct gat gct gtc gga aca aca tgc ggt caa cga ctt gag        1056
Arg Leu Leu Pro Asp Ala Val Gly Thr Thr Cys Gly Gln Arg Leu Glu
            340                 345                 350 aaa gta tac gga aca gag cac tcg gat att ctt cga gta ccc ttc aga        1104
Lys Val Tyr Gly Thr Glu His Ser Asp Ile Leu Arg Val Pro Phe Arg
        355                 360                 365 aca gaa aag gga att gtt cga aaa tgg atc tca aga ttt gaa aaa gtc        1152
Thr Glu Lys Gly Ile Val Arg Lys Trp Ile Ser Arg Phe Glu Lys Val
    370                 375                 380 tgg cca tac ttg gaa acc tac aca gag gat gtt gct cat gaa atc tcc        1200
Trp Pro Tyr Leu Glu Thr Tyr Thr Glu Asp Val Ala His Glu Ile Ser
385                 390                 395                 400 aaa gag ttg cac ggc acg cca gat ctg atc atc gga aac nac agc gac        1248
```

```
Lys Glu Leu His Gly Thr Pro Asp Leu Ile Ile Gly Asn Xaa Ser Asp
            405                 410                 415 ggc aat atc gtc gcc tcc ttg ctc gca cat aaa tta ggt gtc aca cag    1296
Gly Asn Ile Val Ala Ser Leu Leu Ala His Lys Leu Gly Val Thr Gln
        420                 425                 430 tgc acc atc gcc cat gct ttg gag aag aca aaa tat cca gat tca gat    1344
Cys Thr Ile Ala His Ala Leu Glu Lys Thr Lys Tyr Pro Asp Ser Asp
    435                 440                 445 atc tat tgg aag aag ctt gaa gac aaa tac cat ttc tct tgc caa ttt    1392
Ile Tyr Trp Lys Lys Leu Glu Asp Lys Tyr His Phe Ser Cys Gln Phe
450                 455                 460 aca gct gat ctt ttt gca atg aac cat aca gat ttc atc atc acc agt    1440
Thr Ala Asp Leu Phe Ala Met Asn His Thr Asp Phe Ile Ile Thr Ser
465                 470                 475                 480 act ttc cag gaa att gca gga agc aag gac act gtt ggt caa tac gag    1488
Thr Phe Gln Glu Ile Ala Gly Ser Lys Asp Thr Val Gly Gln Tyr Glu
            485                 490                 495 agc cac act gct ttc act ctt cct ggt ctc tac cgt gtt gta cat ggt    1536
Ser His Thr Ala Phe Thr Leu Pro Gly Leu Tyr Arg Val Val His Gly
        500                 505                 510 atc gat gtg ttt gat ccc aaa ttc aac att gtt tcc cct ggt gct gat    1584
Ile Asp Val Phe Asp Pro Lys Phe Asn Ile Val Ser Pro Gly Ala Asp
    515                 520                 525 atg gag ata tac ttc cct tac acc gaa gag aag cgg agg ttg aag cat    1632
Met Glu Ile Tyr Phe Pro Tyr Thr Glu Glu Lys Arg Arg Leu Lys His
530                 535                 540 ttc cat cct gag atc gaa gac ctt ctt tac acc aaa gtt gag aat gaa    1680
Phe His Pro Glu Ile Glu Asp Leu Leu Tyr Thr Lys Val Glu Asn Glu
545                 550                 555                 560 gaa cac tta tgt gtg ctc aat gac cgc aac aag cca att ctg ttc aca    1728
Glu His Leu Cys Val Leu Asn Asp Arg Asn Lys Pro Ile Leu Phe Thr
            565                 570                 575 atg cca agg ctt gat cgt gtc aag aac tta acc gga ctc gtc gag tgg    1776
Met Pro Arg Leu Asp Arg Val Lys Asn Leu Thr Gly Leu Val Glu Trp
        580                 585                 590 tgc ggc aag aac cca aag ttg cgt gag ttg gct aac ctc gta gtt gta    1824
Cys Gly Lys Asn Pro Lys Leu Arg Glu Leu Ala Asn Leu Val Val Val
    595                 600                 605 ggt ggt gat agg cga aag gaa tct aaa gat ttg gaa gag aag gct gaa    1872
Gly Gly Asp Arg Arg Lys Glu Ser Lys Asp Leu Glu Glu Lys Ala Glu
610                 615                 620 atg aag aaa atg ttt gag ctg atc gac aag tac aac ttg aac ggc caa    1920
Met Lys Lys Met Phe Glu Leu Ile Asp Lys Tyr Asn Leu Asn Gly Gln
625                 630                 635                 640 ttc aga tgg ata tca tct caa atg aac aga atc cga aat gtt gaa ctt    1968
Phe Arg Trp Ile Ser Ser Gln Met Asn Arg Ile Arg Asn Val Glu Leu
            645                 650                 655 tac cga tac att tgc gac acg aaa ggt gcc ttt gta cag cct gca ttg    2016
Tyr Arg Tyr Ile Cys Asp Thr Lys Gly Ala Phe Val Gln Pro Ala Leu
        660                 665                 670 tat gaa gcc ttt gga ttg aca gtt gtg gag gca atg act tgc ggt ttg    2064
Tyr Glu Ala Phe Gly Leu Thr Val Val Glu Ala Met Thr Cys Gly Leu
    675                 680                 685 cca aca ttc gca acc tgt aac ggt gga cca gcc gag att att gtc cat    2112
Pro Thr Phe Ala Thr Cys Asn Gly Gly Pro Ala Glu Ile Ile Val His
690                 695                 700 ggg aaa tct ggt ttc aac att gat cct tac cat ggt gat caa gct gct    2160
Gly Lys Ser Gly Phe Asn Ile Asp Pro Tyr His Gly Asp Gln Ala Ala
705                 710                 715                 720
```

-continued

```
gac ata ctc gtc gat ttc ttt gaa aag tgt aag aaa gat cca tct cac    2208
Asp Ile Leu Val Asp Phe Phe Glu Lys Cys Lys Lys Asp Pro Ser His
            725                 730                 735 tgg gat aag atc tcc caa gga ggc ttg aaa cga ata gag gag aag tat    2256
Trp Asp Lys Ile Ser Gln Gly Gly Leu Lys Arg Ile Glu Glu Lys Tyr
        740                 745                 750 aca tgg aag att tac tcg gag aga cta ttg acc ctg aca gga gtg tat    2304
Thr Trp Lys Ile Tyr Ser Glu Arg Leu Leu Thr Leu Thr Gly Val Tyr
    755                 760                 765 gga ttc tgg aag cat gtt tcc aac ctt gaa cgc cgt gag agt cgt cgt    2352
Gly Phe Trp Lys His Val Ser Asn Leu Glu Arg Arg Glu Ser Arg Arg
770                 775                 780 tac ctt gag atg ttt tat gct ctt aag tac cgt aag ctg gct gaa tca    2400
Tyr Leu Glu Met Phe Tyr Ala Leu Lys Tyr Arg Lys Leu Ala Glu Ser
785                 790                 795                 800 gtt cca ttg gca gag gag taa att gaa cct gtt aaa taa cat tgg gcc    2448
Val Pro Leu Ala Glu Glu     Ile Glu Pro Val Lys     His Trp Ala
                805                 810 ggt ttt tct tgg aga ata ata ttc tgt ttt gta att tca att gga gaa    2496
Gly Phe Ser Trp Arg Ile Ile Phe Cys Phe Val Ile Ser Ile Gly Glu
815                 820                 825                 830 gct cct ttg tat ttc atc ttg tct ttt cct ttt cct ttt ttc gcc ggc    2544
Ala Pro Leu Tyr Phe Ile Leu Ser Phe Pro Phe Pro Phe Phe Ala Gly
                835                 840                 845 att gtt tga aca tgg ggt tgt gcg ccc gtc aat tcc agt taa ata tgg    2592
Ile Val     Thr Trp Gly Cys Ala Pro Val Asn Ser Ser     Ile Trp
                850                 855                 860 tga ctt ttg ttt ttc aaa aaa aaa aaa aaa aaa                        2625
    Leu Leu Phe Phe Lys Lys Lys Lys Lys Lys
                865                 870
```

<210> SEQ ID NO 2
<211> LENGTH: 806
<212> TYPE: PRT
<213> ORGANISM: Gossypium hirsutum
<220> FEATURE:
<221> NAME/KEY: misc_feature
<222> LOCATION: (414)..(414)
<223> OTHER INFORMATION: The 'Xaa' at location 414 stands for Asn, Asp, His, or Tyr.
<221> NAME/KEY: misc_feature
<222> LOCATION: (1240)..(1240)
<223> OTHER INFORMATION: n = any nucleotide (a,g,c,t)

<400> SEQUENCE: 2

```
Met Ala Glu Arg Ala Leu Thr Arg Val His Ser Leu Arg Glu Arg Leu
1               5                   10                  15

Asp Glu Thr Leu Leu Ala His Arg Asn Glu Ile Leu Ala Leu Leu Ser
            20                  25                  30

Arg Ile Glu Gly Lys Gly Lys Gly Ile Leu Gln His Gln Ile Ile
        35                  40                  45

Leu Glu Phe Glu Ala Ile Pro Glu Glu Asn Arg Lys Lys Leu Ala Asn
    50                  55                  60

Gly Ala Phe Phe Glu Val Leu Lys Ala Ser Gln Glu Ala Ile Val Leu
65                  70                  75                  80

Pro Pro Trp Val Ala Leu Ala Val Arg Pro Arg Pro Gly Val Trp Glu
                85                  90                  95

Tyr Ile Arg Val Asn Val His Ala Leu Val Val Glu Glu Leu Thr Val
            100                 105                 110

Ala Glu Tyr Leu His Phe Lys Glu Glu Leu Val Asp Gly Ser Ser Asn
        115                 120                 125
```

-continued

```
Gly Asn Phe Val Leu Glu Leu Asp Phe Glu Pro Phe Asn Ser Ser Phe
    130                 135                 140

Pro Arg Pro Thr Leu Ser Lys Ser Ile Gly Asn Gly Val Glu Phe Leu
145                 150                 155                 160

Asn Arg His Leu Ser Ala Lys Leu Phe His Asp Lys Glu Ser Met His
                165                 170                 175

Pro Leu Leu Glu Phe Leu Arg Val His Cys His Lys Gly Lys Asn Met
            180                 185                 190

Met Leu Asn Asp Arg Ile Gln Asn Leu Asn Ala Leu Gln His Val Leu
        195                 200                 205

Arg Lys Ala Glu Glu Tyr Leu Gly Thr Leu Pro Pro Glu Thr Pro Cys
210                 215                 220

Ala Glu Phe Glu His Arg Phe Gln Glu Ile Gly Leu Glu Arg Gly Trp
225                 230                 235                 240

Gly Asp Thr Ala Glu Arg Val Leu Glu Met Ile Gln Leu Leu Leu Asp
                245                 250                 255

Leu Leu Glu Ala Thr Asp Pro Cys Thr Leu Glu Lys Phe Leu Gly Arg
            260                 265                 270

Ile Pro Met Val Phe Asn Val Ile Leu Thr Pro His Gly Tyr Phe
        275                 280                 285

Ala Gln Asp Asn Val Leu Gly Tyr Pro Asp Thr Gly Gly Gln Val Val
290                 295                 300

Tyr Ile Leu Asp Gln Val Arg Ala Leu Glu Asn Glu Met Leu Leu Arg
305                 310                 315                 320

Ile Lys Gln Gln Gly Leu Asn Ile Thr Pro Arg Ile Leu Ile Ile Thr
                325                 330                 335

Arg Leu Leu Pro Asp Ala Val Gly Thr Thr Cys Gly Gln Arg Leu Glu
            340                 345                 350

Lys Val Tyr Gly Thr Glu His Ser Asp Ile Leu Arg Val Pro Phe Arg
        355                 360                 365

Thr Glu Lys Gly Ile Val Arg Lys Trp Ile Ser Arg Phe Glu Lys Val
370                 375                 380

Trp Pro Tyr Leu Glu Thr Tyr Thr Glu Asp Val Ala His Glu Ile Ser
385                 390                 395                 400

Lys Glu Leu His Gly Thr Pro Asp Leu Ile Ile Gly Asn Xaa Ser Asp
                405                 410                 415

Gly Asn Ile Val Ala Ser Leu Leu Ala His Lys Leu Gly Val Thr Gln
            420                 425                 430

Cys Thr Ile Ala His Ala Leu Glu Lys Thr Lys Tyr Pro Asp Ser Asp
        435                 440                 445

Ile Tyr Trp Lys Lys Leu Glu Asp Lys Tyr His Phe Ser Cys Gln Phe
450                 455                 460

Thr Ala Asp Leu Phe Ala Met Asn His Thr Asp Phe Ile Ile Thr Ser
465                 470                 475                 480

Thr Phe Gln Glu Ile Ala Gly Ser Lys Asp Thr Val Gly Gln Tyr Glu
                485                 490                 495

Ser His Thr Ala Phe Thr Leu Pro Gly Leu Tyr Arg Val Val His Gly
            500                 505                 510

Ile Asp Val Phe Asp Pro Lys Phe Asn Ile Val Ser Pro Gly Ala Asp
        515                 520                 525

Met Glu Ile Tyr Phe Pro Tyr Thr Glu Glu Lys Arg Arg Leu Lys His
530                 535                 540
```

-continued

```
Phe His Pro Glu Ile Glu Asp Leu Leu Tyr Thr Lys Val Glu Asn Glu
545                 550                 555                 560

Glu His Leu Cys Val Leu Asn Asp Arg Asn Lys Pro Ile Leu Phe Thr
            565                 570                 575

Met Pro Arg Leu Asp Arg Val Lys Asn Leu Thr Gly Leu Val Glu Trp
        580                 585                 590

Cys Gly Lys Asn Pro Lys Leu Arg Glu Leu Ala Asn Leu Val Val Val
    595                 600                 605

Gly Gly Asp Arg Arg Lys Glu Ser Lys Asp Leu Glu Glu Lys Ala Glu
610                 615                 620

Met Lys Lys Met Phe Glu Leu Ile Asp Lys Tyr Asn Leu Asn Gly Gln
625                 630                 635                 640

Phe Arg Trp Ile Ser Ser Gln Met Asn Arg Ile Arg Asn Val Glu Leu
                645                 650                 655

Tyr Arg Tyr Ile Cys Asp Thr Lys Gly Ala Phe Val Gln Pro Ala Leu
            660                 665                 670

Tyr Glu Ala Phe Gly Leu Thr Val Val Glu Ala Met Thr Cys Gly Leu
        675                 680                 685

Pro Thr Phe Ala Thr Cys Asn Gly Gly Pro Ala Glu Ile Ile Val His
    690                 695                 700

Gly Lys Ser Gly Phe Asn Ile Asp Pro Tyr His Gly Asp Gln Ala Ala
705                 710                 715                 720

Asp Ile Leu Val Asp Phe Phe Glu Lys Cys Lys Lys Asp Pro Ser His
                725                 730                 735

Trp Asp Lys Ile Ser Gln Gly Gly Leu Lys Arg Ile Glu Glu Lys Tyr
            740                 745                 750

Thr Trp Lys Ile Tyr Ser Glu Arg Leu Leu Thr Leu Thr Gly Val Tyr
        755                 760                 765

Gly Phe Trp Lys His Val Ser Asn Leu Glu Arg Arg Glu Ser Arg Arg
    770                 775                 780

Tyr Leu Glu Met Phe Tyr Ala Leu Lys Tyr Arg Lys Leu Ala Glu Ser
785                 790                 795                 800

Val Pro Leu Ala Glu Glu
                805

<210> SEQ ID NO 3
<211> LENGTH: 5
<212> TYPE: PRT
<213> ORGANISM: Gossypium hirsutum
<220> FEATURE:
<221> NAME/KEY: misc_feature
<222> LOCATION: (1240)..(1240)
<223> OTHER INFORMATION: n = any nucleotide (a,g,c,t)

<400> SEQUENCE: 3

Ile Glu Pro Val Lys
1               5

<210> SEQ ID NO 4
<211> LENGTH: 37
<212> TYPE: PRT
<213> ORGANISM: Gossypium hirsutum
<220> FEATURE:
<221> NAME/KEY: misc_feature
<222> LOCATION: (1240)..(1240)
<223> OTHER INFORMATION: n = any nucleotide (a,g,c,t)

<400> SEQUENCE: 4

His Trp Ala Gly Phe Ser Trp Arg Ile Ile Phe Cys Phe Val Ile Ser
```

```
                                          -continued
1                5                10                15
Ile Gly Glu Ala Pro Leu Tyr Phe Ile Leu Ser Phe Pro Phe Pro Phe
                20                25                30

Phe Ala Gly Ile Val
        35

<210> SEQ ID NO 5
<211> LENGTH: 10
<212> TYPE: PRT
<213> ORGANISM: Gossypium hirsutum
<220> FEATURE:
<221> NAME/KEY: misc_feature
<222> LOCATION: (1240)..(1240)
<223> OTHER INFORMATION: n = any nucleotide (a,g,c,t)

<400> SEQUENCE: 5

Thr Trp Gly Cys Ala Pro Val Asn Ser Ser
1               5                   10

<210> SEQ ID NO 6
<211> LENGTH: 10
<212> TYPE: PRT
<213> ORGANISM: Gossypium hirsutum
<220> FEATURE:
<221> NAME/KEY: misc_feature
<222> LOCATION: (1240)..(1240)
<223> OTHER INFORMATION: n = any nucleotide (a,g,c,t)

<400> SEQUENCE: 6

Leu Leu Phe Phe Lys Lys Lys Lys Lys Lys
1               5                   10
```

US 7,498,492 B2

MODIFICATION OF SUCROSE SYNTHASE GENE EXPRESSION IN PLANT TISSUE AND USES THEREFOR

RELATED APPLICATIONS

This application is a continuation-in-part of U.S. Provisional Application Ser. No. 60/251,852, filed Dec. 8, 2000, the contents of which are incorporated herein by reference.

TECHNICAL FIELD

The present invention relates to modifying targeted gene expression in plants to obtain a desired effect in the plant.

BACKGROUND ART

Sucrose synthase (SuSy) is a key enzyme in the breakdown of sucrose in all plant sink tissue, including grain and fruit and has been extensively studied in many plants. Only relatively recently, however, have this protein and gene been characterized from cotton. The full length (2625 bp) of cotton sucrose synthase (SuSy) was isolated by Perez-Grau, L. and Delmer, D. in UC, Davis (accession number U73588) in May 1996. A 2030 bp of the same cDNA with 595 bp missing at the 5' end was isolated by the same group in 1994 and was given to Prem Chourey in USDA/ARS for collaborative research. However, no evidence was available at that time regarding the role of this SuSy gene in cotton fiber/seed development, although it had been speculated (Amor et al., 1995) that part of the fiber localised SuSy could associate with cellulose synthase playing a role to channel carbon to this enzyme.

Evidence has been obtained that the expression of the SuSy gene could be important not only for cellulose synthesis but also for fiber cell initiation (thus may control fuzz) and a model on how sucrose is partitioned and competed for between fiber, seed coat and embryos of the cotton seed was proposed. These work were detailed in the following two papers: Ruan et al., 1997 *Plant Physiology* 115, 375-385; Ruan and Chourey, 1998, *Plant Physiology* 118, 399-406. More recently, the present inventors obtained further evidence supporting the hypothesis that SuSy plays a key role in mobilising sucrose into initiating fiber cells (Ruan et al., 2000 *AJPP* 27, 795-800).

The art is thus deficient in providing methods and means for altering the fiber development and properties in plants, particularly cotton, through alteration of sucrose synthase levels in cells of the plants.

These and other problems are solved as described hereinafter in the different embodiments and claims.

The present inventors have now obtained evidence regarding the role of SuSy in plant development and function through suppressing SuSy expression in transgenic cotton.

SUMMARY OF THE INVENTION

The invention provides a method for altering fiber development or properties of a fiber-producing plant, preferably a cotton plant, particularly a FIBERMAX™ variety comprising the steps of providing cells of said plants with a chimeric gene comprising the following operably linked DNA fragments: a plant expressible promoter, preferably a subterranean clover stunt virus promoter; a coding region which when transcribed yields an RNA said RNA being capable of reducing the expression of an endogenous sucrose synthase gene, preferably an endogenous sucrose synthase gene expressed in fiber cells, preferably fiber initial cells; or capable of being translated into an active sucrose synthase protein; and a transcription termination and polyadenylation signal which functions in the plant cells.

In the embodiments where the RNA is capable of being translated into an active sucrose synthase protein, preferred coding regions comprise a nucleotide sequence selected from the group consisting of: (a) a nucleotide sequence encoding a polypeptide comprising the amino acid sequence of SEQ ID No 2; (b) a nucleotide sequence comprising the nucleotide sequence of SEQ ID No 1; (c) a nucleotide sequence having at least 70% sequence identity with the nucleotide sequence a) or b); and (d) a nucleotide sequence hybridizing under stringent conditions with the nucleotide sequence (a) or (b); or a part thereof encoding an active sucrose synthase.

In the embodiments where the RNA is capable of reducing the expression of an endogenous sucrose synthase gene, preferred coding regions comprise a nucleotide sequence selected from the group consisting of: a nucleotide sequence comprising at least 19 or 25 contiguous nucleotides having at least 70% sequence identity to a nucleotide sequence encoding a polypeptide comprising the amino acid sequence of SEQ ID No 2 or the complement thereof; and a nucleotide sequence comprising at least 19 or 25 contiguous nucleotides having at least 70% sequence identity from a nucleotide sequence encoding a polypeptide comprising the amino acid sequence of SEQ ID No 1 or the complement thereof, particularly where the coding region comprises the nucleotide sequence of SEQ ID No 1 from the nucleotide at position 2208 to the nucleotide at position 2598 or the complement thereof. The coding region may comprise simultaneously both sense and antisense nucleotide sequences capable of forming a double stranded RNA molecule.

It is another objective of the invention to provide a method for improving fiber yield in a fiber-producing plant, comprising providing cells of said plant with a chimeric gene comprising the following operably linked DNA fragments: a plant expressible promoter; a DNA region capable of being translated into an active sucrose synthase protein; a transcription termination and polyadenylation signal which functions in said plant cells.

The invention also provides a method for improving fiber quality in a fiber-producing plant, comprising providing cells of said plant with a chimeric gene comprising the following operably linked DNA fragments a plant expressible promoter;

A DNA region capable of being translated into an active sucrose synthase protein a transcription termination and polyadenylation signal which functions in said plant cells.

In yet another embodiment of the invention a method is provided for increasing seed size in a fiber-producing plant, comprising providing cells of said plant with a chimeric gene comprising the following operably linked DNA fragments a seed-specific promoter; a DNA region capable of being translated into an active sucrose synthase protein; a transcription termination and polyadenylation signal which functions in said plant cells.

The invention also relates to fiber-producing plants, particularly cotton plants, comprising in their genome a chimeric DNA comprising the following operably linked DNA fragments: a plant expressible promoter; a coding region which when transcribed yields an RNA, said RNA being capable of reducing the expression of an endogenous sucrose synthase gene, preferably an endogenous sucrose synthase gene expressed in fiber cells, preferably fiber initial cells; or capable of being translated into an active sucrose synthase protein; a transcription termination and polyadenylation signal which functions in said plant cells.

Yet another objective of the invention is to provide a fiber-producing plant comprising a chimeric DNA according to the invention wherein said RNA is capable of increasing the expression of an endogenous sucrose synthase gene, preferably an endogenous sucrose synthase gene expressed in fiber cells, preferably fiber initial cells and said fiber cells have an increased sucrose synthase activity compared to fiber cells of plant cells which do not comprise said chimeric DNA.

In yet another embodiment of the invention fiber-producing plants are provided comprising a chimeric DNA according to the invention, wherein said coding region comprises a nucleotide sequence selected from (a) a nucleotide sequence encoding a polypeptide comprising the amino acid sequence of SEQ ID No 2; (b) a nucleotide sequence comprising the nucleotide sequence of SEQ ID No 1; (c) a nucleotide sequence having at least 70% sequence identity with the nucleotide sequence (a) or (b); and (d) a nucleotide sequence hybridizing under stringent conditions with the nucleotide sequence (a) or (b); or a part thereof encoding an active sucrose synthase.

The invention also provides a fiber-producing plant comprising the chimeric genes of the invention wherein said RNA is capable of reducing an endogenous sucrose synthase gene and said fiber cells have a reduced sucrose synthase activity compared to fiber cells of plant cells which do not comprise said chimeric DNA, particularly wherein the coding region comprises a nucleotide sequence selected from the group consisting of a nucleotide sequence comprising at least 19 or 25 contiguous nucleotides having at least 70% sequence identity to a nucleotide sequence encoding a polypeptide comprising the amino acid sequence of SEQ ID No 2 or the complement thereof; and a nucleotide sequence comprising at least 19 or 25 contiguous nucleotides having at least 70% sequence identity from a nucleotide sequence encoding a polypeptide comprising the nucleotide sequence of SEQ ID No 1 or the complement thereof, particularly wherein the coding region comprises the nucleotide sequence of SEQ ID No 1 from the nucleotide at position 2208 to the nucleotide at position 2598 or the complement thereof.

Also provided are seeds of a fiber-producing plant, preferably cotton plant comprising the chimeric DNA or genes according the invention as well as fibers with altered development or properties, isolated from such plants.

The invention also relates to the use of a sucrose synthase encoding nucleotide sequence for altering fiber yield or fiber quality or fiber properties.

BRIEF DESCRIPTION OF THE DRAWINGS

FIG. 8C represents the regression analysis between SuSy activity and fiber length.

DETAILED DESCRIPTION OF THE INVENTION

Figure 1:
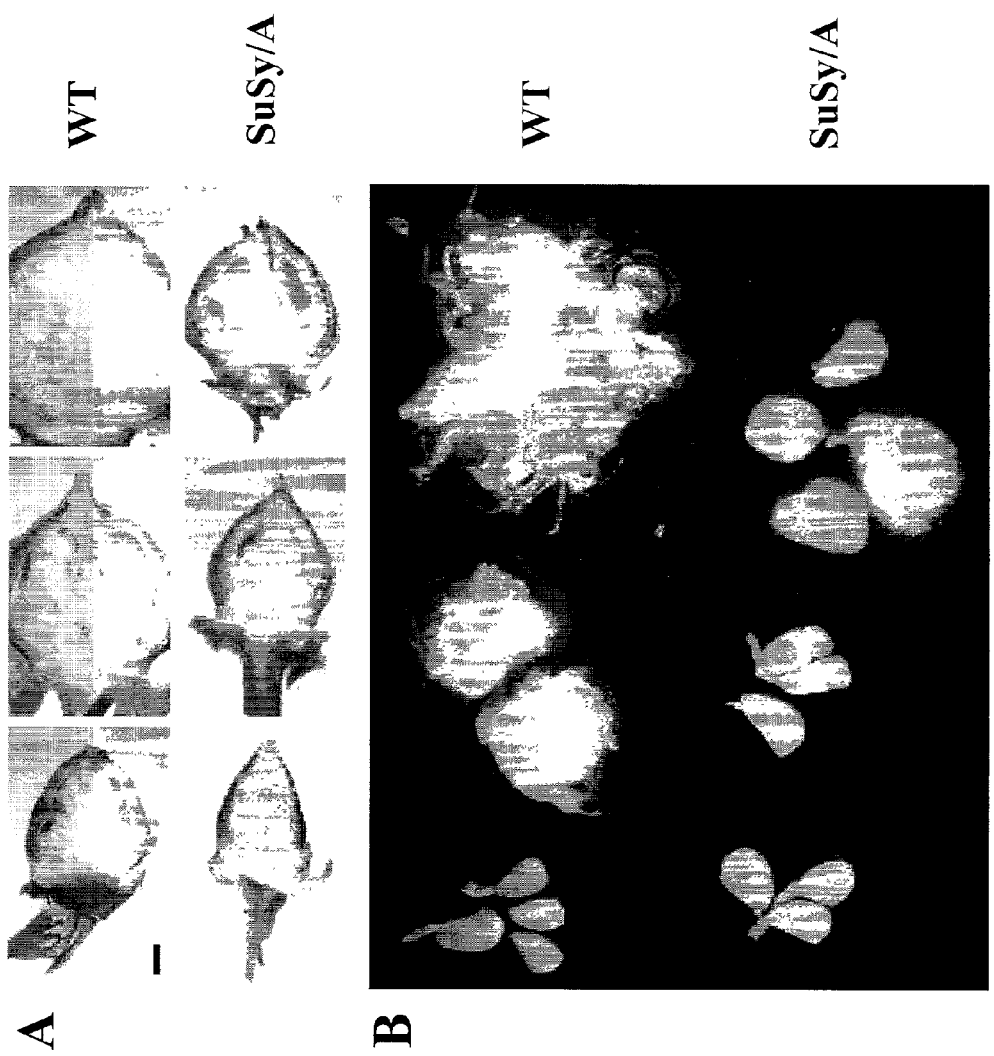
FIG. 1 illustrates that down regulation of SuSy in the fiber causes a decrease in fiber elongation in transgenic plants. Three developmental stages are shown: 0, 2 and 6 days after anthesis.

In a first aspect, the present invention provides a plant having altered expression of an isoform of sucrose synthase (SuSy) resulting in an altered fiber, fruit or seed production ability.

Preferably, the plant is a transgenic plant having an under- or overexpression of an isoform of SuSy involved in fruit/seed production. In a preferred form, the plant retains expression of SuSy in developing vegetative tissue such that growth and development of the plant is not adversely affected.

When the plant undergoes underexpression of an isoform of SuSy involved in fruit/seed production, the plant has a reduced fiber or seed production. When the plant undergoes overexpression of an isoform of SuSy involved in fruit/seed production, the plant has an enhanced fiber or seed production.

The ability to cause underexpression of an isoform of SuSy involved in fruit/seed production can be used to develop plants that produce few or no seeds but are still able to grow and produce fruit normally. The ability to cause overexpression of an isoform of SuSy involved in fruit/seed production in a tissue specific manner can be used to develop plants which produce greater amounts of fiber or longer fiber or having altered fiber structure but are still able to grow and develop normally. The plant can be any plant where expression of an isoform of SuSy is involved in fruit/seed production. The present invention is applicable for modifying a wide range of horticultural crops such as grape, peach, pear, and apple. More preferably, the plant is a cotton plant.

In a preferred embodiment, plants, particularly cotton plants, are provided comprising a chimeric gene, preferably stably integrated in their genome, the chimeric gene comprising the following operably linked DNA fragments:

a plant expressible promoter
a coding region which when transcribed yields an RNA which is either
   capable of reducing the expression of an endogenous sucrose synthase gene, preferably an endogenous sucrose synthase gene expressed in fiber initial cells; or
   capable of being translated into an active sucrose synthase protein; and
a transcription termination and polyadenylation signal which functions in plant cells.

A particularly preferred embodiment of the coding region as defined above is a coding region comprising a nucleotide sequence which encodes a protein comprising the amino acid of SEQ ID 2, particularly the nucleotide sequence of SEQ ID No 1, or a part of such a nucleotide sequence capable of being translated into a functional sucrose synthase. The coding region encoding the sucrose synthase activity may be derived from other plant species or other species (as indicated elsewhere in this application) and may be, e.g., from potato (cDNA sequence is available from Genbank library, accession number M18745).

A particularly preferred embodiment of the coding region as defined above is a coding region comprising the complement of a nucleotide sequence ("antisense") encoding a polypeptide encoded by the nucleotide sequence of SEQ ID No 1 from the nucleotide at position 2208 to the nucleotide at position 2598, particularly the coding region comprises the nucleotide sequence of SEQ ID No 1 from the nucleotide at position 2208 to the nucleotide at position 2598.

As used herein, a "coding region refers" to a DNA sequence which is capable of being transcribed into a biologically active RNA. Biologically active RNA includes RNA which is capable of inducing a biological effect in the target cell, such as antisense or sense RNA capable of triggering post transcriptional gene silencing, ribozymes etc.

Biologically active RNA also includes RNA that is capable of being translated into a polypeptide or protein.

Having read these preferred embodiments, the person skilled in the art will immediately realize that functional equivalents of the mentioned coding regions may be used to similar effect.

Functional equivalents of a coding region capable of being transcribed into RNA that is capable of reducing the expression of an endogenous sucrose synthase gene include e.g. smaller antisense fragments of the mentioned nucleotide sequences.

The length of the antisense nucleotide sequence may vary from about 10 nucleotides (nt) or 19 nt, up to a length equaling the length (in nucleotides) of the target nucleic acid (here a sucrose synthase gene). Preferably the total length of the antisense nucleotide sequence is at least 10 nt, preferably 15 nt or 19 nt, particularly at least about 50 nt, more particularly at least about 100 nt, especially at least about 150 nt, more especially at least about 200 nt, quite especially at least about 500 nt. It is expected that there is no upper limit to the total length of the antisense nucleotide sequence, other than the total length of the target nucleic acid. However for practical reason (such as e.g. stability of the chimeric genes) it is expected that the length of the antisense nucleotide sequence should not exceed 5000 nt, particularly should not exceed 2500 nt and could be limited to about 1000 nt.

It will be appreciated that the longer the total length of the antisense nucleotide sequence is, the less stringent are the requirements for sequence identity between the total antisense nucleotide sequence and the complement of the corresponding sequence in the target sucrose synthase gene. Preferably, the total antisense nucleotide sequence should have a sequence identity of at least about 75% with the complement corresponding target sequence, particularly at least about 80%, more particularly at least about 85%, quite particularly about 90%, especially about 95%, more especially about 100%, quite especially be identical to complement of the corresponding part of the target nucleic acid. However, it is preferred that the antisense nucleotide sequence always includes a sequence of about 10 consecutive nucleotides, particularly about 19 or 20 nt, more particularly about 50 nt, especially about 100 nt, quite especially about 150 nt with 100% sequence identity to the complement of the corresponding part of the target nucleic acid. Preferably, for calculating the sequence identity and designing the corresponding antisense sequence, the number of gaps should be minimized, particularly for the shorter antisense sequences.

Particularly preferred are antisense nucleotide sequences having a sequence identity of at least about 75%, preferably at least about 80%; particularly at least about 85%; quite particularly about 90%, especially about 95% with the complement of the corresponding part of the nucleotide sequence of SEQ ID No 1.

For the purpose of this invention, the "sequence identity" of two related nucleotide or amino acid sequences, expressed as a percentage, refers to the number of positions in the two optimally aligned sequences which have identical residues ($\times 100$) divided by the number of positions compared. A gap, i.e. a position in an alignment where a residue is present in one sequence but not in the other is regarded as a position with non-identical residues. The alignment of the two sequences is performed by the Needleman and Wunsch algorithm (Needleman and Wunsch 1970). Computer-assisted sequence alignment, can be conveniently performed using standard software program such as GAP which is part of the Wisconsin Package Version 10.1 (Genetics Computer Group, Madison, Wis., USA) using the default scoring matrix with a gap creation penalty of 50 and a gap extension penalty of 3.

It is also understood that sense fragments may be used for reducing the expression of an endogenous sucrose synthase gene, and the same embodiments of length and sequence homology as herein described for antisense molecules, apply mutatis mutandis to the sense molecules.

Particularly suited for reducing the expression of an endogenous sucrose synthase genes are DNA regions, preferably under the control of a plant-expressible promoter, which when transcribed result in so-called double stranded RNA molecules, comprising both sense and antisense sequences which are capable of forming a double stranded RNA molecule as described in WO 99/53050 (herein entirely incorporated by reference). In this particular case, a chimeric gene may thus be introduced into a plant cell comprising a plant expressible promoter operably linked to a DNA region, whereby that DNA region comprises a part of coding region comprising at least 10 or 19 consecutive nucleotides from the coding region of a nucleic acid encoding a sucrose synthase protein, such as but not limited to, a sucrose synthase protein with the amino acid sequence of SEQ ID No 1 (the so-called sense part) as well as a DNA sequence which comprises at least the complementary DNA sequence of at least 10 or 19 nucleotides of the sense part, but which may be completely complementary to the sense part (the so-called antisense part). The chimeric gene may comprise additional regions, such as a transcription termination and polyadenylation region functional in plants. When transcribed an RNA can be produced which may form a double stranded RNA stem between the complementary parts of the sense and antisense region. A spacer region may be present between the sense and antisense nucleotide sequence. The chimeric gene may further comprise an intron sequence, preferably located in the spacer region.

Functional equivalents of coding regions capable of being transcribed into RNA that can be translated into an active sucrose synthase comprise mutant or allelic forms derived from sucrose synthase genes, particularly from sucrose synthase gene with active expression in fiber initials.

Methods to derive mutants e.g. of a sucrose synthase gene, particularly of sucrose synthase genes encoding a protein as represented in SEQ ID 2, quite particularly of sucrose synthase gene comprising the nucleotide sequence of SEQ ID 1, such a site-specific mutagenesis methods are well known in the art, as well as assays to identify active sucrose synthase enzymes encoded by the mutant sequences.

Allelic forms of the nucleotide sequences encoding sucrose synthase may be identified by hybridization of libraries, under stringent conditions, such as cDNA or genomic libraries of a different varieties or plant lines, particularly cotton varieties and plant lines. Nucleotide sequences which hybridize under stringent conditions to nucleotide sequences encoding the amino acid sequence of SEQ ID 2 or to the nucleotide sequence of SEQ ID 1, or a sufficiently large part thereof (preferably about 25 contiguous nucleotides, particularly at least about 50 contiguous nucleotides, more particularly at least about 100 contiguous nucleotides) and which encode a functional protein with sucrose synthase activity are functional equivalents of the above mentioned preferred coding regions. Such nucleotides may also be identified and isolated using e.g. polymerase chain reaction amplification using an appropriate pair of oligonucleotides having at least about 25 contiguous nucleotides, particularly at least about 50 contiguous nucleotides, more particularly at least about 100 contiguous nucleotides of the nucleotide of SEQ ID No 1.

"Stringent hybridization conditions" as used herein mean that hybridization will generally occur if there is at least 95% and preferably at least 97% sequence identity between the probe and the target sequence. Examples of stringent hybridization conditions are overnight incubation in a solution comprising 50% formamide, 5×SSC (150 mM NaCl, 15 mM trisodium citrate), 50 mM sodium phosphate (pH 7.6), 5×Denhardt's solution, 10% dextran sulfate, and 20 µg/ml denatured, sheared carrier DNA such as salmon sperm DNA, followed by washing the hybridization support in 0.1×SSC at approximately 65° C. Other hybridization and wash conditions are well known and are exemplified in Sambrook et al, Molecular Cloning: A Laboratory Manual, Second Edition, Cold Spring Harbor, N.Y. (1989), particularly chapter 11.

The following are accession numbers of nucleotide sequences in the Genbank library which are plant sucrose synthase genes, parts thereof or nucleotide sequences having sequence similarity to sucrose synthase genes which could be used according to the methods herein described: BM094593 (*Glycine max*); BM093753 (*Glycine max*); BM093158 (*Glycine max*); BM092695 (*Glycine max*); BM092443 (*Glycine max*); BM092322 (*Glycine max*); BM085310 (*Glycine max*); BM085020 (*Glycine max*); AY059416 (*Zea mays*); AF273253 (*Beta vulgaris*); L39940 (*Oryza sativa*); AJ316590 (*Nostoc punctiforme*); AJ316589 (*Nostoc punctiforme*); AJ316596 (Anabaena sp.); AJ316595(Anabaena sp.); AJ316584 (Anabaena sp.); BM005654 (*Crocus sativus*); BI973032 (*Glycine max*); BI971794 (*Glycine max*); AF367450 (*Prunus persica*); BI945506 (*Glycine max*); BI944973 (*Glycine max*); AF420224 (*Carica papaya*); BI788449 (*Glycine max*); BI788359 (*Glycine max*); BI787127 (*Glycine max*); BI787033(*Glycine max*); BI787000 (*Glycine max*); BI786823(*Glycine max*); BI784933 (*Glycine max*); BI784627 (*Glycine max*); BI700214 (*Glycine max*); BI699934 (*Glycine max*); BI699923 (*Glycine max*); BI699585(*Glycine max*); BI543240 (Sugar beet); BI498340 (*Glycine max*); BI471463 (*Glycine max*); BI427241 (*Glycine max*); BI427174 (*Glycine max*); BI427022 (*Glycine max*); BI426915 (*Glycine max*); AF393809 (*Apium graveolens*); BI321173 (*Glycine max*); BI320832 (*Glycine max*); BI316894 (*Glycine max*); BI316826 (*Glycine max*); BI316405 (*Glycine max*); BI315949 (*Glycine max*); BI203222 (*Lycopersicon esculentum*); BI176503 (*Solanum tuberosum*); BG273882 (Grape berries); AY034958 (*Arabidopsis thaliana*); AF378187 (*Oryza sativa*); BG790580 (*Glycine max*); BG790079 (*Glycine max*); BG726150 (*Glycine max*); BG654021 (*Glycine max*); BG653916 (*Glycine max*); BG653624 (*Glycine max*); BG652711 (*Glycine max*); BG652507 (*Glycine max*); BG649914 (*Glycine max*); BG649831 (*Glycine max*); AJ309093 (*Pinus pinaster*); BG507656 (*Glycine max*); BG405632 (*Glycine max*); BG405474 (*Glycine max*); BG405204 (*Glycine max*); BG405017 (*Glycine max*); BG363730 (*Glycine max*); BG362638 (*Glycine max*); BG359764 (*Glycine max*); BG359452 (*Glycine max*); BG359307 (*Glycine max*); AJ311496 (*Pisum sativum*); BG239317 (*Glycine max*); BG237287 (*Glycine max*); BG157592 (*Glycine max*); BG 155900 (*Glycine max*); BG047402 (*Glycine max*); BG046717 (*Glycine max*); BG046686 (*Glycine max*); BG046043 (*Glycine max*); BG043243 (*Glycine max*); BG042159 (*Glycine max*); BG041814 (*Glycine max*); AB045710 (*Pyrus pyrifolia*); BF597682 (*Glycine max*); BF597330 (*Glycine max*); BF597258 (*Glycine max*); BF595837 (*Glycine max*); BF595646 (*Glycine max*); BF425609 (*Glycine max*); BF423725 (*Glycine max*); BF324657 (*Glycine max*); BF154308 (*Solanum tuberosum*); BF154187 (*Solanum tuberosum*); BF154037 (*Solanum tuberosum*); BF153500 (*Solanum tuberosum*); BF153341 (*Solanum tuberosum*); BF153335 (*Solanum tuberosum*); BF153307 (*Solanum tuberosum*); BF097021 (*Lycopersicon esculentum*); BF070782 (*Glycine max*); BF070666 (*Glycine max*); BF070277 (*Glycine max*); BF070188 (*Glycine max*); BF068815 (*Glycine max*); BF071174 (*Glycine max*); BF067110 (*Glycine max*); BF009756 (*Glycine max*); BE806119 (*Glycine max*); BE805996 (*Glycine max*); BE805178 (*Glycine max*); BE800976 (*Glycine max*); BE800941 (*Glycine max*); BE800227 (*Glycine max*); BE611805 (*Glycine max*); BE611493 (*Glycine max*); BE610447 (*Glycine max*); BE610325 (*Glycine max*); BE609887(*Glycine max*); BE609881 (*Glycine max*); BE607382 (*Oryza sativa*); BE607326 (*Oryza sativa*); BE607323 (*Oryza sativa*); BE556484 (*Glycine max*); BE556306 (*Glycine max*); BE555319 (*Glycine max*); AJ001117 (*Triticum aestivum*); AJ292758 (*Anabaena variabilis*); BE474178 (*Glycine max*); BE440931 (*Glycine max*); BE440323 (*Glycine max*); BE347277 (*Glycine max*); AF263384 (*Saccharum officinarum*); BE330345 (*Glycine max*); BE211050 (*Glycine max*); BE209707 (*Glycine max*); AW561929 (*Gossypium hirsutum*); BE040389 (*Oryza sativa*); BE040121 (*Oryza sativa*); BE039563 (*Arabidopsis thaliana*); BE034387 (*Mesembryanthemum crystallinum*); BE033387 (*Mesembryanthemum crystallinum*); BE023957 (*Glycine max*); BE023630 (*Glycine max*); BE022760 (*Glycine max*); BE021167 (*Glycine max*); BE020760 (*Glycine* max); BE020591 (Glycine max); BE020550 (Glycine max); AW990923 (Euphorbia esula); AW832022 (Glycine max); AW760552 (Glycine max); AW756812 (Glycine max); AW756072 (Glycine max); AW756065 (Glycine max); AW734901(Glycine max); AW707163 (Glycine max); AW706660 (Glycine max); AW706520 (Glycine max); AW706203 (Glycine max); AW705595 (Glycine max); AW704619 (Glycine max); AB025778 (Citrus unshiu); AB021745 (Citrus unshiu); AW666333 (Glycine max); AW666277 (Glycine max); AW666250 (Glycine max); AW620859 (Glycine max); AW598476 (Glycine max); AW598473 (Glycine max); AW597690 (Glycine max); AW597373 (Glycine max); AW597332 (Glycine max); AW596993 (Glycine max); AW570615 (Glycine max); AW570577 (Glycine max); AW570566 (Glycine max); AW570513 (Glycine max); AW569822 (Glycine max); AW568526 (Glycine max); AW568333 (Glycine max); AW509231 (Glycine max); AW472408 (Glycine max); AW459606 (Glycine max); AW458318 (Glycine max); X82504 (C. rubrum); AW432731 (Glycine max); AW432392 (Glycine max); AW432192 (Glycine max); AW397142 (Glycine max); AW397071 (Glycine max); AW309503 (Glycine max); AW307502 (Glycine max); AW307391 (Glycine max); AW307001 (Glycine max); AW306834 (Glycine max); AB018561 (Citrullus lanatus); AB029401 (Citrus unshiu); AB022092 (Citrus unshiu); AB022091 (Citrus unshiu); AW279073 (Glycine max); AW279053 (Glycine max); AW278487 (Glycine max); AJ388994 (Medicago truncatula); AJ388888 (Medicago truncatula); AW234887 (Glycine max); AJ238219 (Triticum aestivum); AJ238218 (Triticum aestivum); AJ238217 (Triticum speltoides); AW201670 (Glycine max); AW185801 (Glycine max); AW185627 (Glycine max); AJ249624 (Triticum aestivum); AJ249623 (Triticum aestivum); AW164630 (Glycine max); AW164393 (Glycine max); AW133248 (Glycine max); AW101578 (Glycine max); AW100191 (Glycine max); AW100069 (Glycine max); AW099557 (Glycine max); X96938 (T. gesneriana); X96939 (T. gesneriana); AW035186 (Lycopersicon esculentum); AW033439 (Lycopersicon esculentum); AW032339 (Lycopersicon esculentum); AJ132002 (Craterostigma plantagineum); AJ 132001 (Craterostigma plantagineum); AJ132000 (Craterostigma plantagineum); AJ131999 (Craterostigma plantagineum); AI973811 (Glycine max); AI973710 (Glycine max); AI973540 (Glycine max); AI967739 (Lotus japonicus); AI965972 (Glycine max); AI960742 (Glycine max); AI960703 (Glycine max); AI930917 (Glycine max); AI900130 (Glycine max); AI900087 (Glycine max); AI855470 (Glycine max); AA080634 (Saccharum sp.); AA080610 (Saccharum sp.); AA269294 (Saccharum sp.); AA080580 (Saccharum sp.); AI736370 (Glycine max); AI731292 (Gossypium hirsutum); AI731115 (Gossypium hirsutum); AI729201 (Gossypium hirsutum); AI728436 (Gossypium hirsutum); AI727966 (Gossypium hirsutum); AI726092 (Gossypium hirsutum); U73588 (Gossypium hirsutum); U73587 (Gossypium hirsutum); AJ002080 (Pisum sativum); AJ131964 (Medicago truncatula); AJ131943 (Medicago truncatula); AJ133726 (Lotus japonicus); Y16091 (Daucus carota); Y16090 (Daucus carota); AJ001319 (Lycopersicon esculentum); AI496671 (Glycine max); AI496540 (Glycine max); AI496532 (Glycine max); AI495774 (Glycine max); AI495135 (Glycine max); AI495023 (Glycine max); AI494833 (Glycine max); AJ011534 (Lycopersicon esculentum); Y15802 (Hordeum vulgare); AI461126(Glycine max); AI460757 (Glycine max); AI460629 (Glycine max); AI444096 (Glycine max); AI444083 (Glycine max); AI444054 (Glycine max); AI443620 (Glycine max); AI443476 (Glycine max); AI443231 (Glycine max); AI442789 (Glycine max); AI442411 (Glycine max); AI441989 (Glycine max); AI441004 (Glycine max); AI1437923 (Glycine max); AI437907 (Glycine max); AI437840 (Glycine max); AJ010639 (Anabaena sp.); AJ011535 (Lycopersicon esculentum); D10266 (Vigna radiata); L03366 (Oryza sativa); AF030231 (Glycine max); M97551 (Vicia faba); AJ000153 (Triticum aestivum); AF079523 (Musa acuminata); AF079851 (Pisum sativum); AJ001071 (Pisum sativum); AF049487 (Medicago sativa); AF054446 (Mesembryanthemum crystallinum); AA753339 (Oryza sativa); AA752298 (Oryza sativa); AA752293 (Oryza sativa); M753445 (Oryza sativa); AA753437 (Oryza sativa); AA753297 (Oryza sativa); M752123 (Oryza sativa); AA751990 (Oryza sativa); M750692 (Oryza sativa); AA750079 (Oryza sativa); AA749692 (Oryza sativa); AA749554 (Oryza sativa); AA720478 (Mesembryanthemum crystallinum); M661050 (Medicago truncatula); M661041 (Medicago truncatula); AA660686 (Medicago truncatula); D88412 (Cotton); D10418 (Rice); D21308 (Rice); D29733 (Rice); X81974 (B. vulgaris); X92378 (A. glutinosa); Z56278 (V. faba); Z48640 (V. faba); X98598 (P. sativum); T25261 (Zea mays); T23326 (Zea mays); T14713 (Zea mays); T14662 (Zea mays); T14661 (Zea mays); X75332 (D. carota); X02382 (Zea mays); X02400 (Zea mays); X70990 (A. thaliana); X60987 (A. thaliana); X69773 (V. faba); X73477 (S. tuberosum); Z11532 (S. officinarum); Z15028 (O. sativa); X64770 (O. sativa); X59046 (O. sativa); X66728 (H. vulgare); X65871 (H. vulgare); X69931 (H. vulgare); A27685 (O. sativa); W21612 (Zea mays); U24088 (Solanum tuberosum); U24087 (Solanum tuberosum); X73221 (H. vulgare); L32898 (Zea mays); F13913 (Arabidopsis thaliana); F13912 (Arabidopsis thaliana); U21129 (Solanum tuberosum); M26672 (Triticum aestivum); M26671 (Triticum aestivum); L19762 (Lycopersicon esculentum); M18745 (Potato); L33244 (Zea mays); L22296 (Zea mays); and Z17959 (Arabidopsis thaliana). These sequences are incorporated by reference.

In a second aspect, the present invention provides a method of altering the production of fiber, fruit or seeds in a plant, the method comprising causing under- or overexpression of an isoform of SuSy involved in fruit/seed production in the plant.

Preferably, for underexpression, the method involves providing a genetic construct that targets the 3' end of the SuSy gene when transformed in a plant. The construct can be a co-suppression antisense or combined sense/antisense (inverted repeat) SuSy construct.

In a third aspect, the present invention provides a plant having an altered ability to produce fiber, fruit or seeds produced by the method according to the second aspect of the present invention.

In a fourth aspect, the present invention provides a genetic construct targeting the 3' end of the SuSy gene which, when expressed in a plant, reduces the expression of an isoform of SuSy involved in fruit/seed production.

Preferred embodiments of the chimeric genes, particularly of the coding regions used for these methods are as described elsewhere in this specification.

Figure 5:
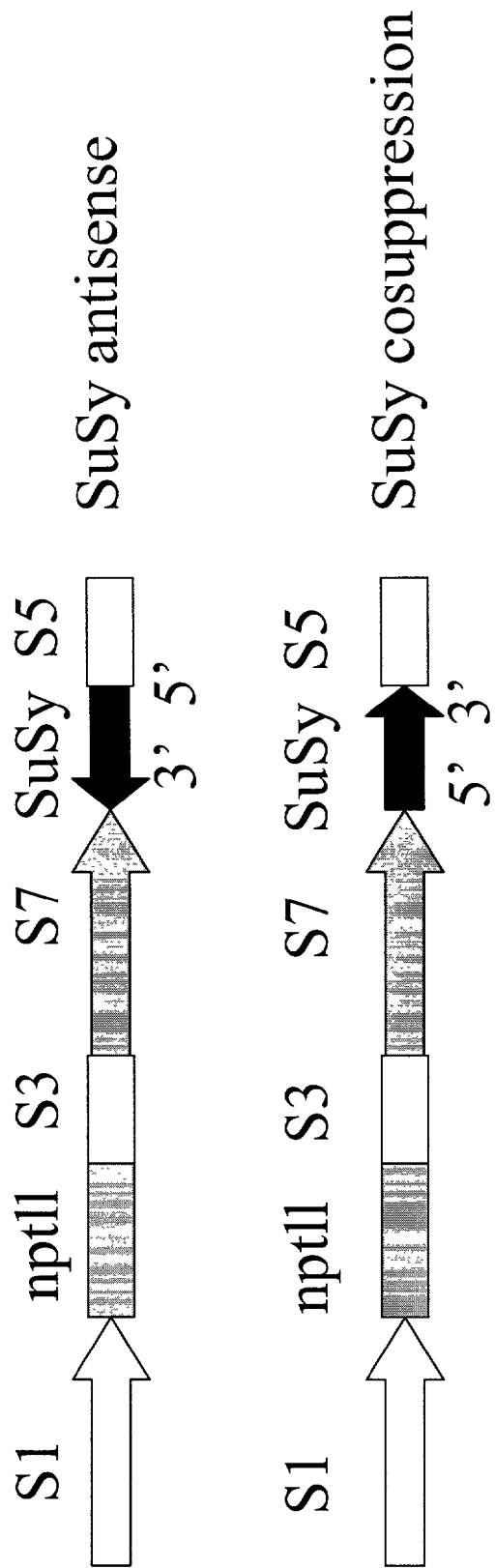
FIG. 5 shows construct maps used for SuSy suppression. Note nptII is neomycin phosphotransferase marker gene for selection of transformants and S1, S7 and S3, S5 designate the promoters and terminators respectively encoded by the subclover stunt-virus (see Australian Patent No 689311). "SUSY" represents the 390 bp nucleotide sequence of a sucrose synthase cDNA (available at Genbank under the Accession number U73588) from CTGGGAT to TGACTT (211 bp coding region upstream of the stop codon plus 179 bp 3' UTR region; nucleotide sequence of SEQ ID 1 from the nucleotide at position 2208 to the nucleotide at position 2598).

Preferably, the construct is selected from the constructs shown in FIG. 5, a combination of parts of both constructs to generate an inverted repeat gene suppression construct, with or without a tissue specific promoter region.

One preferred method of developing constructs is by using the "pPLEX" technology involving subclover stunt virus promoters and terminators described in AU 689311.

In a fifth aspect, the present invention provides use of the construct according to the fourth aspect of the present invention to produce a plant having reduced ability to produce fiber, fruit or seeds.

The present invention is suitable for the following applications:

A) Use of SuSy to improve fiber yield

SuSy may be used to improve fiber synthesis by increasing SuSy expression or activity in such plant cells, e.g., a fiber specific or fiber enhanced promoter (such as but not limited to a cotton expansion promoter, or the promoter of the SuSy gene having the nucleotide sequence of SEQ ID No 1), or a constitutive promoter (such as CaMV 35S) can be used to express the SuSy gene in cotton cells.

Cotton fiber yield can be improved by reducing or suppressing cotton fuzz fiber. Fuzz fiber specific or enhanced promoter or constitutive promoter to reduce sucrose synthase selectively in cotton fuzz fiber cells. Reduced expression can be achieved by gene silencing technologies (antisense, co-suppression, dominant negative etc). Dominant negative mutant alleles of sucrose synthase genes may be obtained, e.g., through mutation (insertion, substitution, or deletion of the phosphorylation site(s) of the sucrose synthase protein coding region)

Cotton fiber yield can be improved by modifying fuzz fibers into lint fibers, e.g., by expression of SuSy coding region or a functional equivalent thereof by fiber specific or fiber enhanced promoter, primary or secondary cell wall promoter or a constitutive promoter.

B) Use of SuSy gene to improve fiber quality

Fiber length is an example of fiber quality. Expression of SuSy by a fiber specific or fiber enhanced promoter, primary cell wall promoter or a constitutive promoter.

C) Use of SuSy to improve fiber properties (e.g. fiber strength, length and number)

Fiber strength is an example of a fiber property. Fiber strength is significantly affected by the cellulose content in the secondary cell wall of fiber cells. This may be achieved by expression of SuSy by a fiber specific or fiber enhanced promoter, secondary cell wall promoter or a constitutive promoter.

D) Overexpression of SuSy, specifically in seeds, to increase sucrose utilization in seeds for increased seed size and storage product content.

E) Overexpression in the maternal tissue of a fruit (such as cotton fiber, horticultural fruit) for increased carbohydrate or fiber content.

F) Suppression of SuSy in seed with over expression of SuSy in fruit/fiber for increased fiber/fruit yield.

Preferred plant-expressible promoters include the fiber specific and/or secondary cell wall specific promoters which can be isolated according to the teaching of WO 98/18949, WO 98/00549 or U.S. Pat. No. 5,932,713.

The correlation of sucrose synthase activity in the ovule epidermis of cotton with fiber length also allows the use of sucrose synthase proteins (or antibodies or aptamers recognizing the same) or sucrose synthase coding regions as a diagnostic tool in cotton breeding. These may be used to identify cotton lines or varieties, including wild sources, which have enhanced sucrose synthase activity and increased potential to form longer fibers, particularly when crossed in a breeding program with other cotton lines and/or varieties having good fiber characteristics. Nucleic acids derived from sucrose synthase coding regions may be used to determine the amount of sucrose synthase RNA in the ovule epidermis. In addition, polymorphisms, including single nucleotide polymorphisms between sucrose synthase genes may be used to identify lines with superior sucrose synthase alleles.

Throughout this specification, unless the context requires otherwise, the word "comprise", or variations such as "comprises" or "comprising", will be understood to imply the inclusion of a stated element, integer or step, or group of elements, integers or steps, but not the exclusion of any other element, integer or step, or group of elements, integers or steps.

The methods and means of the invention are particularly suited for use in cotton plants, (both *Gossypium hirsutum* and *Gossypium barbadense*) particularly for Coker 312, Coker 310, Coker 5Acala SJ-5, GSC25110, FiberMax 819, Siokra 1-3, T25, GSA75, Acala SJ2, Acala SJ4, Acala SJ5, Acala SJ-C1, Acala B1644, Acala B1654-26, Acala B1654-43, Acala B3991, Acala GC356, Acala GC510, Acala GAM1, Acala C1, Acala Royale, Acala Maxxa, Acala Prema, Acala B638, Acala B1810, Acala B2724, Acala B4894, Acala B5002, non Acala "picker" Siokra, "stripper" variety FC2017, Coker 315, STONEVILLE 506, STONEVILLE 825, DP50, DP61, DP90, DP77, DES119, McN235, HBX87, HBX191, HBX107, FC 3027, CHEMBRED A1, CHEMBRED A2, CHEMBRED A3, CHEMBRED A4, CHEMBRED B1, CHEMBRED B2, CHEMBRED B3, CHEMBRED C1, CHEMBRED C2, CHEMBRED C3, CHEMBRED C4, PAYMASTER 145, HS26, HS46, SICALA, PIMA S6 and ORO BLANCO PIMA.

Any description of prior art documents herein is not an admission that the documents form part of the common general knowledge of the relevant art.

In order that the present invention may be more clearly understood, preferred forms will be described with reference to the following examples and drawings.

MODES FOR CARRYING OUT THE INVENTION

Definitions

General Molecular Biology

Unless otherwise indicated, the recombinant DNA techniques utilized in the present invention are standard procedures, well known to those skilled in the art. Such techniques are described and explained throughout the literature in sources such as, J. Perbal, A Practical Guide to Molecular Cloning, John Wiley and Sons (1984); J. Sambrook et al., Molecular Cloning: A Laboratory Manual, Cold Spring Harbor Laboratory Press (1989); T. A. Brown (editor), Essential Molecular Biology: A Practical Approach, Volumes 1 and 2, IRL Press (1991); D. M. Glover and B. D. Hames (editors), DNA Cloning: A Practical Approach, Volumes 1-4, IRL Press (1995 and 1996); and F. M. Ausubel et al. (Editors), Current Protocols in Molecular Biology, Greene Pub. Associates and Wiley-Interscience (1988, including all updates until present). These publications are incorporated herein by reference.

Analysis for presence of the transgene by Southern blotting was carried out as described in Sambrook et al. (1989) and immunolocalization of the SuSy protein was carried out on tissue sections as described in Ruan and Chourey (1998).

Gene/DNA Isolation

The DNA encoding a protein may be obtained from any cDNA library prepared from tissue or organisms believed to express the gene mRNA and to express it at a detectable level. The gene sequences can also be obtained from a genomic library or genomic DNA.

Libraries are screened with probes or analytical tools designed to identify the gene of interest or the protein encoded by it. For cDNA expression libraries, suitable probes include monoclonal or polyclonal antibodies that recognize and specifically bind the protein; oligonucleotides of about 20-80 bases in length that encode known or suspected portions of cDNA from the same or different species; and/or complementary or homologous cDNAs or fragments thereof that encode the same or a hybridizing gene. Appropriate probes for screening genomic DNA libraries include, but are not limited to, oligonucleotides; cDNAs or fragments thereof that encode the same or hybridizing DNA including expressed sequence tags and the like; and/or homologous genomic DNAs or fragments thereof. Screening the cDNA or genomic library with the selected probe may be conducted using standard procedures as described in chapters 10-12 of Sambrook et al.

An alternative means to isolate a gene encoding is to use polymerase chain reaction (PCR) methodology as described in section 14 of Sambrook et al. This method requires the use of oligonucleotide probes that will hybridize to the gene.

The oligonucleotide sequences selected as probes should be of sufficient length and sufficiently unambiguous that false positives are minimized. The actual nucleotide sequence(s) is usually based on conserved or highly homologous nucleotide sequences or regions of the gene. The oligonucleotides may be degenerate at one or more positions. The use of degenerate oligonucleotides may be of particular importance where a library is screened from a species in which preferential codon usage in that species is known. The oligonucleotide must be labeled such that it can be detected upon hybridization to DNA in the library being screened. The preferred method of labeling is to use $^{32}$P-labelled ATP with polynucleotide kinase, as is well known in the art, to radiolabel the oligonucleotide. However, other methods may be used to label the oligonucleotide, including, but not limited to, biotinylation or enzyme labeling.

Nucleic acid having all the protein coding sequence is obtained by screening selected cDNA or genomic libraries, and if necessary, using conventional primer extension procedures as described in section 7.79 of Sambrook et al., to detect precursors and processing intermediates of mRNA that may not have been reverse-transcribed into cDNA.

Another alternative method for obtaining the gene of interest is to chemically synthesize it using one of the methods described in Fingels et al. (*Agnew Chem. Int. Ed. Engl.* 28: 716-734, 1989). These methods include triester, phosphite, phosphoramidite and H-Phosphonate methods, PCR and other autoprimer methods, and oligonucleotide syntheses on solid supports. These methods may be used if the entire nucleic acid sequence of the gene is known, or the sequence of the nucleic acid complementary to the coding strand is available, or alternatively, if the target amino acid sequence is known, one may infer potential nucleic acid sequences using known and preferred coding residues for each amino acid residue.

Cotton Transformation

Cotton was transformed using an Agrobacterium-mediated transformation technique as described in F. Murray et al. 1999 (*Molec. Breeding* 5: 219-232). Transformed plants were grown in a glasshouse under natural illumination at day/night temperatures of approximately 30° C./22° C.

EXAMPLE 1

SuSy-Suppression in Cotton

Figure 6:
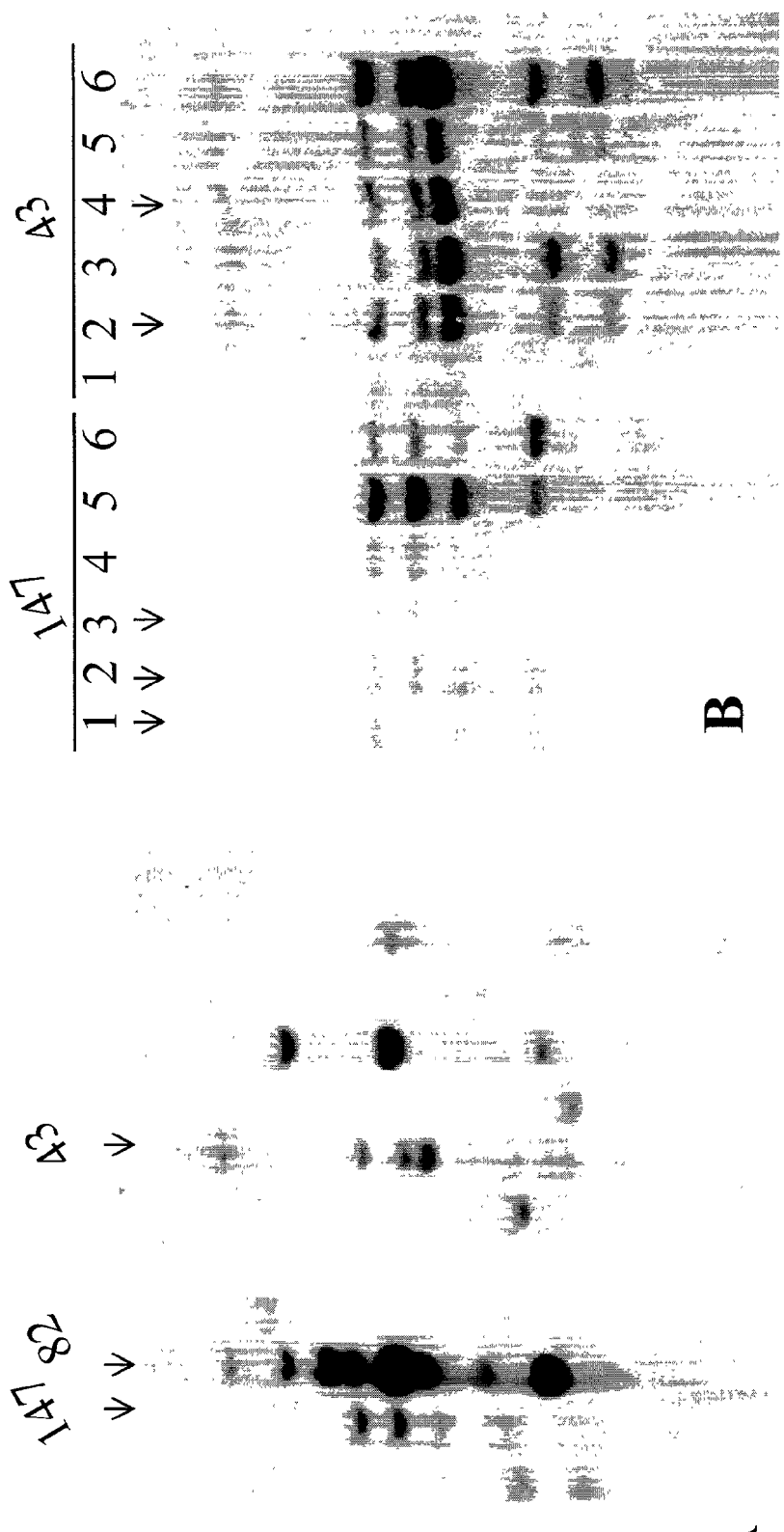
FIG. 6 represents Southern blot hybridization results on DNA isolated from T0 generation plants (A) and segregating plants of the T1 generation plants (B) respectively. The arrows indicate lines with fiber-less phenotypes. The numbers indicate the transgenic cotton line number to which the individual plants belong.

To provide evidence regarding the role of SuSy in fiber development, the present inventors transformed cotton with co-suppression and antisense SuSy constructs, targeting the 3' end of the seed SuSy cDNA driven by a constitutive sub-clover stunt seven virus promoter (see FIG. 5 for a schematic representation). The presence of the transgene in 11 transgenic lines so far was confirmed by Southern analysis (see FIG. 6). Among them two antisense lines (294-147, 292-43) and one co-suppression line (295-82) showed dramatic reductions in fiber and seed development with the remaining lines showing various degrees of inhibition of fiber growth.

Figure 2:
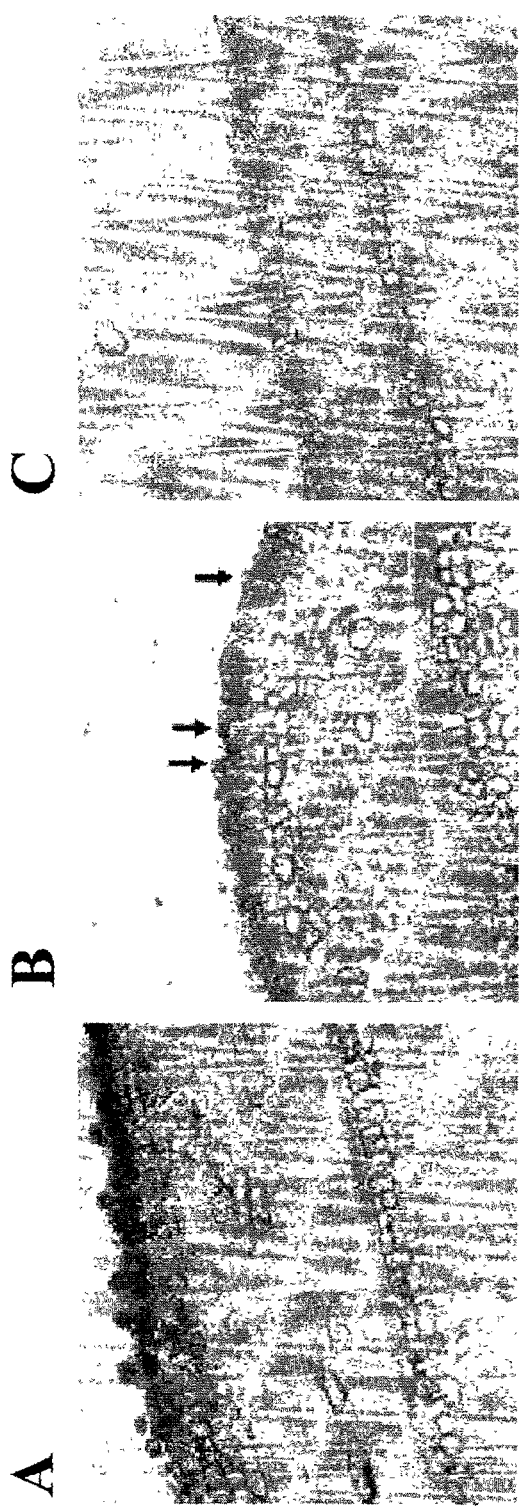
FIG. 2 is an immunolocalization to detect SuSy protein level. Note black labelling in the wild type (WT) in developing fiber cells on surface of ovule and in ovule epidermis. Transgenic lines show reduced amount of SuSy protein (less black label) and in 295-82, no SuSy protein. This correlates with lack of fiber development.
Figure 3:
FIG. 3 shows transgenic lines where SuSy is also reduced in the embryo (upper boll and seeds). Seeds are fiberless but note the great reduction in seed size in III. Some seeds did not form at all.
Figure 3:
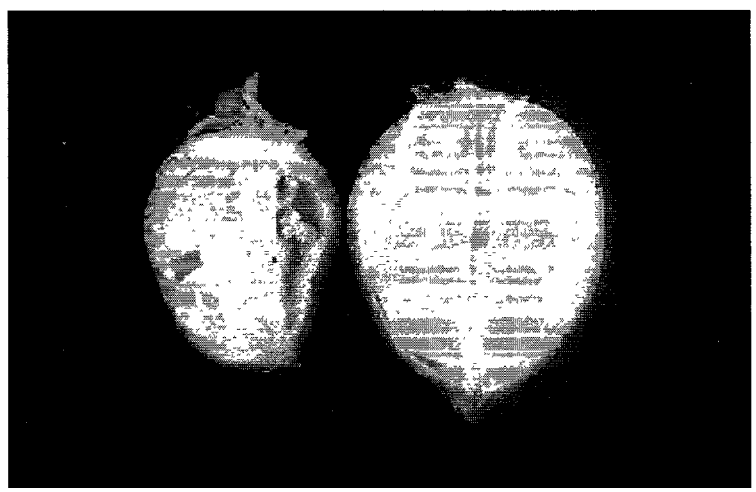
Figure 4:
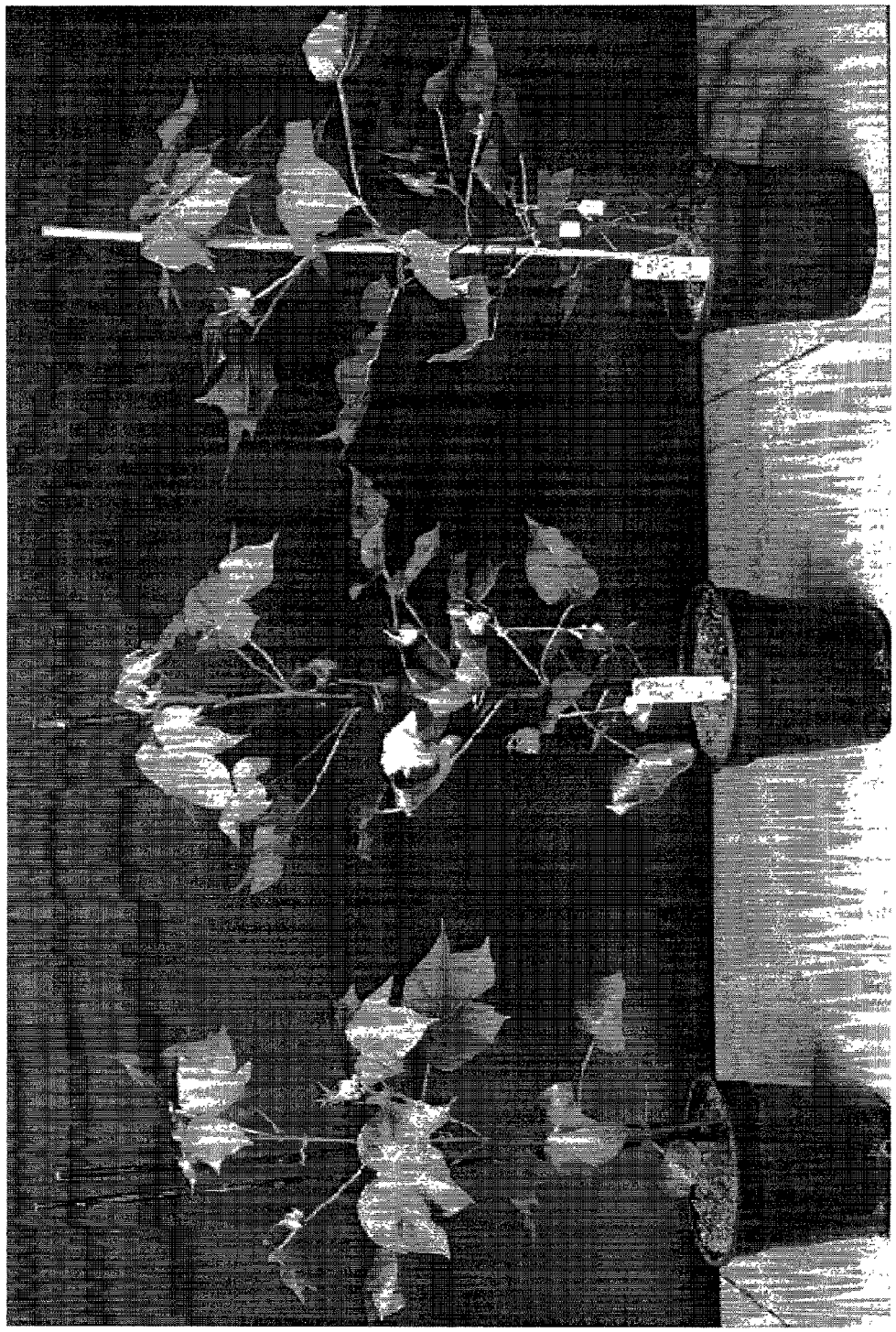
FIG. 4 shows that there was no effect of the transgene on vegetative growth. (WT on left and two typical transgenic lines).

It was found that:

(a) Immunolocalization analysis on 0-d ovule sections (FIG. 2) revealed that, compared to wild type fiber initials, SuSy protein was reduced to less than 20% wild type levels in fibers of line 294-147 and to undetectable levels in 295-82. Furthermore, the number and size of initiating fibers was reduced by at least 50% in these two lines as compared that in the wild type ovules. Indeed, by 6 days after anthesis (DAA), these transgenic seeds were virtually fiber-less (see FIG. 1). Sucrose synthase activity was determined biochemically. Whereas WT plants show a SuSy activity of 22.5 nmol/min/seed, line 147 showed a SuSy activity of 5.8 nmol/min/seed and line 82 showed no detectable activity. This led to a dramatic reduction of normal fiber initial cells in the ovule epidermis. It is clear from these results that the degree of fiber initiation depends on the level of SuSy expression in the ovule epidermis.

Figure 7:
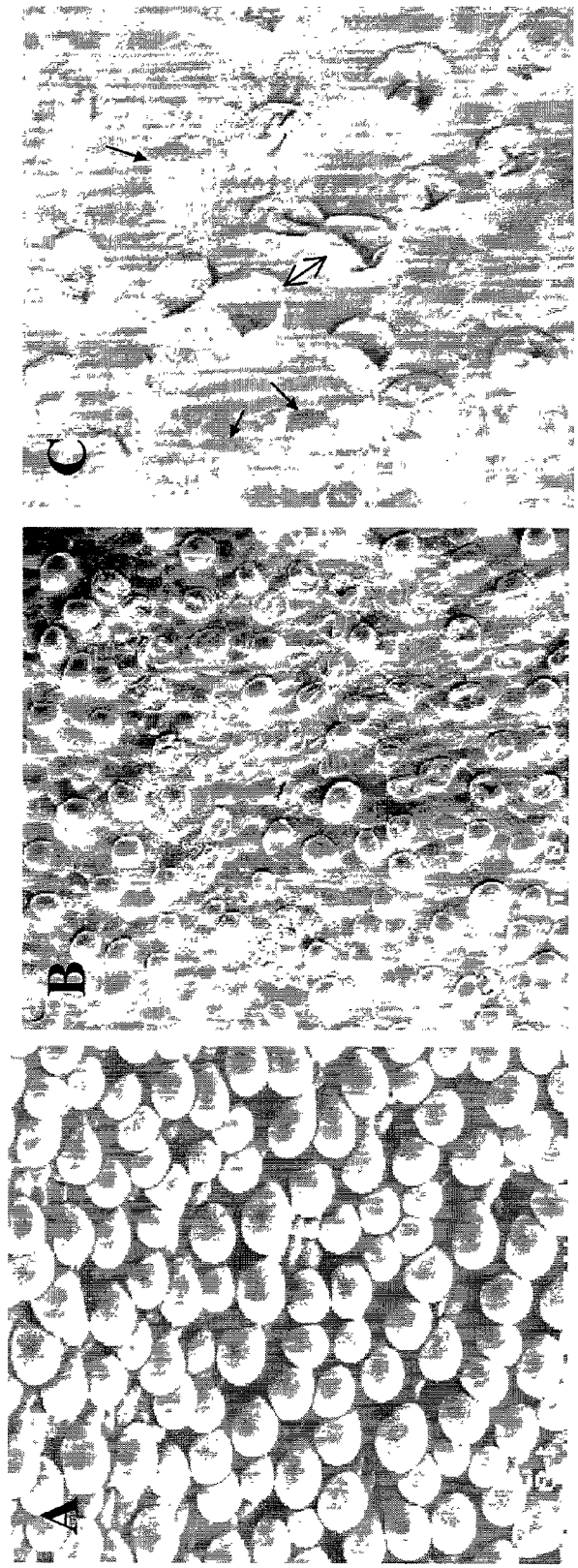
FIG. 7 is a scanning electron microscopy (SEM) analysis on ovule epidermis of line 147 in FIG. 2B. Many fiber cells are collapsed and shrunk, some fiber cells popped up but were much smaller and less in number (FIG. 7B) when compared to the wild type (FIG. 7A) ovule. The shrunk and collapsed phenotype was clearly demonstrated under high magnification (FIG. 3C).

The impact of SuSy expression on fiber initiation is further demonstrated by scanning electron microscopy analysis of the ovule epidermis of line 147 (see FIG. 7) revealed that many fiber cells are collapsed and shrunk (see FIG. 7B). Some fiber cells appeared, but these were much smaller, and were reduced in number when compared to wild type ovule (FIG. 7A). The shrunk and collapsed phenotype was clearly visible under high magnification (FIG. 7C).

These results demonstrate that some isoforms of SuSy play a critical role in fiber initiation and elongation. Suppression of an isoform of SuSy can thus be used to prevent or reduce fiber initiation and elongation while overexpression can thus be used to enhance fiber initiation and elongation.

(b) While all the bolls in line 295-82 and 292-43 dropped off prematurely by 10 DAA, some bolls of line 294-147 were retained to maturity. In those mature bolls, most seeds were stunted, shrunken and fiberless. About 15% of the seeds, however, showed 30% of the wild type fiber length (loose fiber as well) and wild type embryo and seed size, most likely due to segregation of the transgene.

This demonstrates that suppression of isoforms of SuSy in the maternal tissue (seed coat/fiber) alone can inhibit fiber development by ~70% in length, while additional repression of SuSy in the embryo can arrest seed development entirely.

Gene suppression of isoforms of SuSy in the embryo specifically to give a seedless phenotype (in a wide range of horticultural crops such as grape, peach, pear, apple).

(c) Line 292-43 and 295-82 were male-sterile (no pollen) and the seed set can be recovered by pollination with wild-type pollen. This shows SuSy plays a role in male sterility of cotton.

Gene suppression of SuSy in male floral parts was found to cause sterility. Sucrose synthase activity, the fresh weight of pollen and viability of the pollen were tested on developing anthers 2 days before flowering in different lines. The viability assay was conducted by staining with 2,3,5-triphenyltetrazolium chloride (TTC). The results are summarized in Table 1.

TABLE 1

Suppression of SuSy in anthers leads to male sterility by pollen formation inhibition.

| Line | SuSy activity (nmol min$^{-1}$ mg$^{-1}$) | Pollen fresh weight (% of WT pollen per anther) | Viable pollen (% of 100 grains) |
|---|---|---|---|
| WT | 44.1 ± 1.1 | 100.0 | 85.2 |
| 147#1 | 29.5 ± 6.9 | 30.0 | 52 |
| 147#2 | 14.7 ± 0.9 | 0.0 | 0.0 |
| 82 | 18.2 ± 1.5 | 0.0 | 0.0 |

A reduction of SuSy activity in anthers by about 33% results in an about 70% reduction of total pollen weight, largely due to the reduction in the amount of pollen produced. Of the residual 30%, only half of the pollen was viable. When SuSy was reduced by about 60%, no pollen was formed. Pollen development is thus very sensitive to changes in SuSy activity. Pollen formation can thus be influenced (inhibited or promoted) by suppressing or overexpressing SuSy in anthers.

Figure 9:
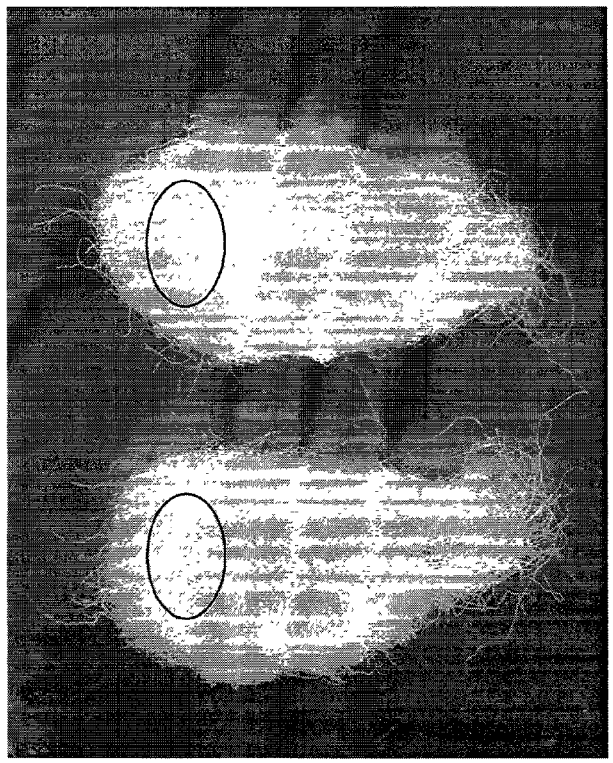
FIG. 9 is a figure showing reduced fuzz length in SuSy suppressed transgenic line 147#2 (panel B) compared to wild type (panel B). The seeds were delinted by hand. The oval represents the chalazal end of the mature seeds. Seeds covered by fuzz of the transgenic line appear browner than the wild type seeds, because the underlying brown seed coat is covered by shorter fuzz fiber.
Figure 9:
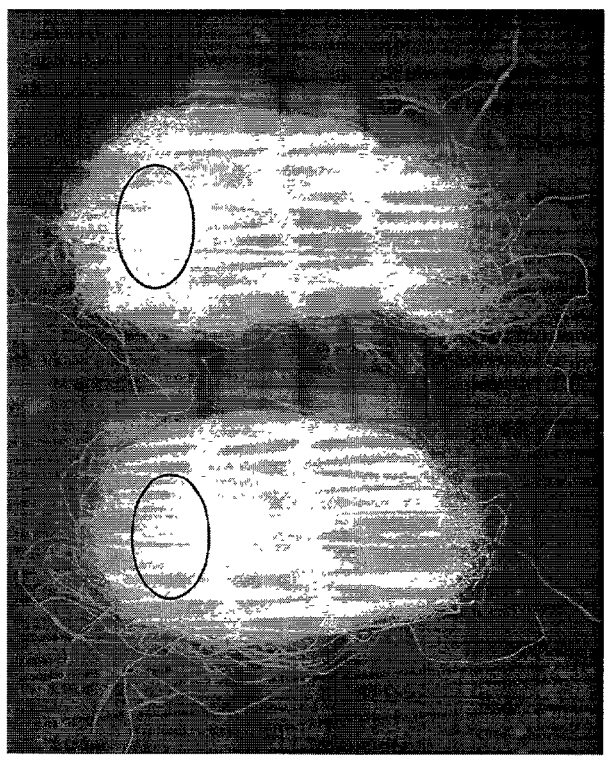

Suppression of SuSy activity in the maternal seed coat tissue in the transgenic cotton plants also led to reduced fuzz length in the SuSy suppressed transgenic plants when compared to a wild type plant (see FIG. 9). Fuzz fiber length was measured from the chalazal end of the mature seeds and the measurement was done by gently stretching the fuzz of seeds, delinted by hand, and measuring the length from the seed coat epidermis to the tip. The brown color visible in the transgenic line is because fuzz is shorter in transgenic lines than in WT, where the brown seed coat is well covered by relatively long fuzz. SuSy activity was also determined. The results can be summarized as follows:
- the wild type plant had a fuzz length of 2.2 mm (and a SuSy activity measurement set at 100%)
- transgenic line 147#2 had a fuzz length of 1.4 mm (and a SuSy activity measurement of 36% of the WT).

From the gene suppression experiments, it will be understood that overexpression of SuSy gene will have potential beneficial effects on fiber, fruit and seed production in plants.

EXAMPLE 2

Further Analysis of Progeny of Cotton Lines 82, 147 and 43 with Suppressed SuSy Activity To confirm the correlation between the presence of the SuSy suppression transgene and the reduced fiber initiation in cotton, further analysis was conducted on the T1 generation. About 24 T1 seeds were sown from six T0 lines. All germinated seedlings were screened by PCR for presence or absence of the transgenes (nptII; S7 promoter and SuSy suppression transgene). Six PCR positive and one PCR negative segregating individuals from each of the six lines were further analysed on molecular biochemical and cellular level. Line 82 was propagated vegetatively as a reference point. The fiber-less phenotype in the different lines of the T0 generation (indicated by arrows in FIG. 6A) was still preserved in respectively three and two segregating individuals of the T1 generation for line 147 and 43 respectively (arrows in FIG. 6B). The remaining individuals show various degree of fiber/seed suppression. The vegetatively kept line 82 continues to produce fiberless seeds. These results demonstrated that the fiberless/or seed suppressed phenotype described was indeed due to the presence of SuSy transgene.

Figure 8:
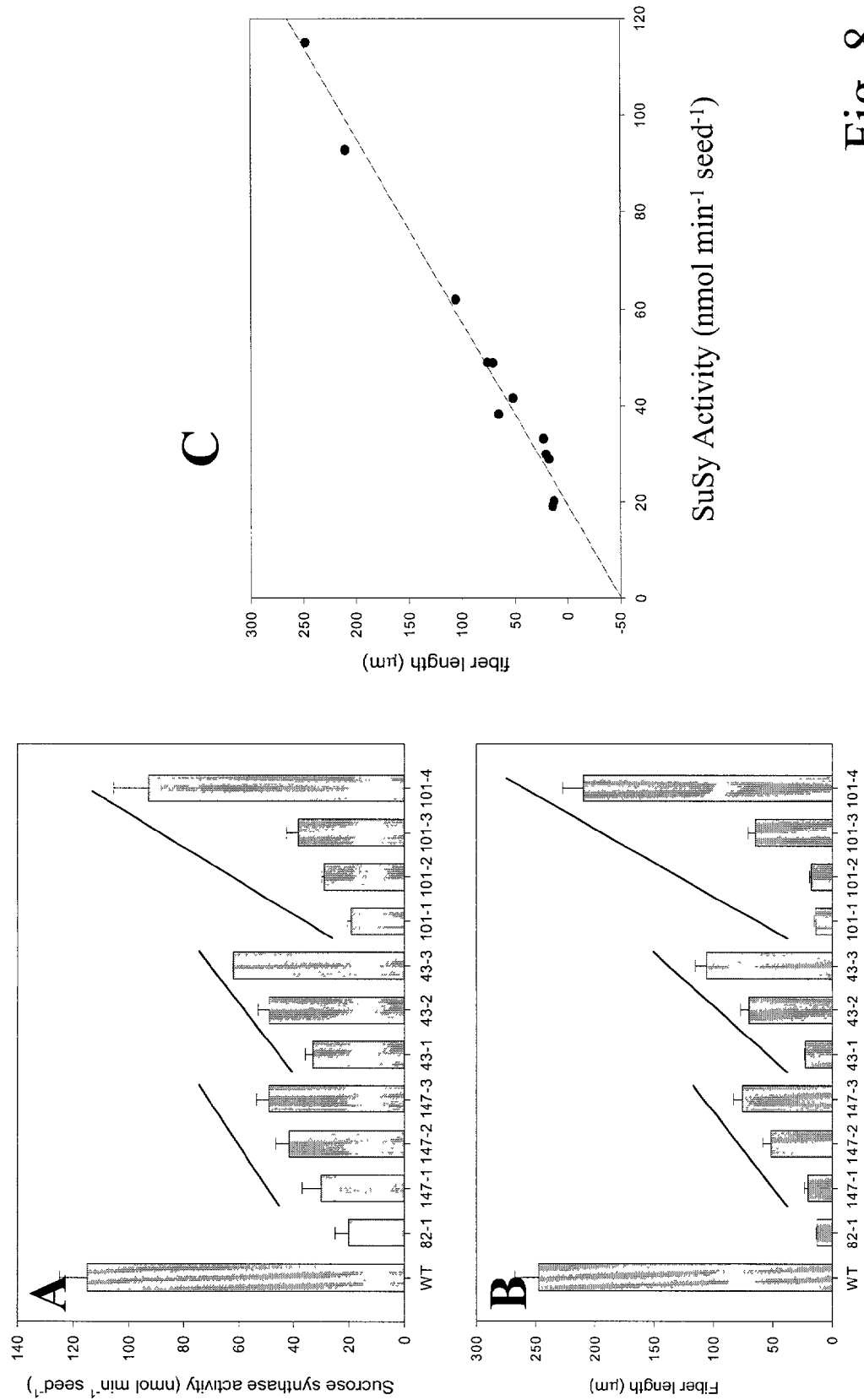
FIG. 8 shows the correlation between changes of SuSy activity (FIG. 8A) and reduction of fiber length (FIG. 8B) in 3-day-old seeds from 10 segregating individuals of three T1 generation lines (lines 147, 43 and 101), together with line 82 and wild type (WT).

A positive strong correlation could be found between the degree of sucrose activity in the seed epidermis and the fiber length in segregating T1 generation plants of lines 147, 43 and 101 (see FIG. 8). When fiber length was plotted against sucrose synthase activity for the different plants of the different lines as well as the wild type line, a linear regression could be derived (Y=2.634X-50; $R^2$=0.98). The linear nature of the correlation up to the wild-type level, indicates that overexpression of the sucrose synthase activity above wild type level will lead to fiber length greater than fiber length in wild type plants.

A similar strong correlation exists between the reduction in SuSy activity and mature cotton fiber length and dry weight. SuSy activity in seed coat epidermis has been reduced to 28.8%, 42.5% and 53.9% of the wild type level in segregating individuals #1, #2 and #3 of line 43 T1 generation plants respectively. Lint fiber dry weight per boll was 11.1%, 51.6%, and 70.9% respectively.

Cellulose content in cotton fiber is also closely correlated to the level of SuSy expression. Cellulose content was analysed by labeling cotton fiber at day 25 (peak of cellulose synthesis in vivo) with Calcofluor white, a fluorescent dye specifically binding to cellulose. The fluorescent intensity of the labeled fibers, indicating cellulose content, was significantly reduced in the SuSy-suppressed transgenic lines when compared to fluorescence in the wild type. The degree of fluorescence reduction correlated to the degree of suppression of SuSy activity.

EXAMPLE 3

Overexpression of Sucrose Synthase in Cotton Plants

The coding sequence of a potato sucrose synthase cDNA (Genbank Accession number M18745) is operably linked to a subterranean clover stunt virus promoter (S7; WO9606932) and a 3' transcription termination and polyadenylation signal functional in plants. This chimeric gene is operably linked to a selectable marker gene and introduced into a T-DNA vector. Cotton plants are transformed using the above-mentioned Agrobacterium-mediated transformation technique. Transgenic cotton lines are identified; sucrose synthase activity, fiber length, fuzz fiber length, cellulose content, and dry weight of the lint are analyzed. A positive correlation is found between SuSy activity and increased fiber length cellulose content, and dry weight of the lint.

SUMMARY OF THE EXAMPLES

The single-cell cotton fibers initiate from ovule epidermis at anthesis, elongate to 2.5~3.0 cm in about 16 days and then synthesize massive amounts of cellulose. Thus, cotton fiber is an excellent system for the study of cell differentiation, elongation and cellulose synthesis in higher plants with significant industry implications for improving fiber yield and quality.

To provide definitive evidence regarding the role of SuSy in fiber and seed development, the present inventors transformed cotton with co-suppression and antisense SuSy constructs, targeting the 3' end of the seed SuSy cDNA driven by subclover stunt seven virus promoter. The presence of the transgene in nine transgenic lines so far was confirmed by Southern analysis. Among them one antisense line (294-147) and one co-suppression line (295-82) showed dramatic reductions in fiber and seed development with the remaining lines showing various degrees of inhibition of fiber growth. Immunolocalization analysis on 0-d ovule sections revealed that, compared to wild type fiber initials, SuSy protein was reduced to only about 20% of wild-type levels in fibers of line 294-147 and to undetectable levels in 295-82. Furthermore, the number and size of initiating fibers was reduced by at least 50% in these two lines as compared that in the wild-type ovules. Indeed, by 2 d after anthesis (DAA), these transgenic seeds were virtually fiberless. This is in contrast to a fiber-covered seed phenotype seen in the wild type plants at this stage. While all the bolls in line 295-82 dropped off prematurely by 10 DAA, some bolls of line 294-147 were retained to maturity. In those mature bolls, most seeds were stunted, shrunken and fiberless. About 15% of the seeds, however, showed 30% of the wild type fiber length and wild type embryo and seed size, most likely due to segregation of the transgene. These results demonstrate (a) that SuSy plays a critical role in fiber initiation and elongation, and (b) that suppression of SuSy in the maternal tissue (seed coat/fiber) alone can inhibit fiber development while additional repression of SuSy in the embryo can arrest seed development entirely. The influence of SuSy suppression on the reduction of fiber length has been confirmed by analysis of progeny of the transgenic cotton lines. Further, a linear correlation was found between the level of SuSy activity and the increase in fiber length. The linear nature of this correlation indicates that in wild type cotton, the level of sucrose synthase is limiting.

Overexpression of sucrose synthase at least in maternal ovule tissue increases fiber length in fiber-producing plants.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

REFERENCES

Amor, Y., Haigler, C. H., Johnson, S., Wainscott, M. and Delmer, D. P. (1995) A membrane associated form of sucrose synthase and its potential role in synthesis of cellulose and callose in plants. *Proc Nat Acad Science USA* 92: 9353-9357.

Ruan, Y. -L., Llewellyn, D. J, Furbank, R. T. (2000) Pathway and control of sucrose import into initiating fiber cells. *Australian Journal of Plant Physiology* 27:795-800.

Ruan, Y. -L. and Chourey, P. S. (1998) A fiberless seed (fls) mutation in cotton is associated with lack of fiber cell initiation in ovule epidermis, alteration in sucrose synthase expression and carbon partitioning in developing seed. *Plant Physiology* 118: 399-406

Ruan, Y. -L., Chourey, P. S., Delmer, D. P. and Luis, P. G. (1997) The differential expression of sucrose synthase in relation to diverse patterns of carbon partitioning in developing cotton seed. *Plant Physiology* 115: 375-385

We claim:

1. A method to increase fiber length of a cotton plant comprising the step of providing cells of a cotton plant with a chimeric gene comprising the following operably linked DNA fragments:
   a plant expressible promoter selected from a constitutive promoter, a subclover stunt virus promoter, a fiber specific promoter, a primary cell wall promoter or a secondary cell wall promoter;
   the coding region from a plant sucrose synthase gene; and,
   a transcription termination and polyadenylation signal which functions in said plant cells.

2. The method according to claim 1, wherein said coding region from a plant sucrose synthase gene is translated into an active plant sucrose synthase protein.

3. The method according to claim 1, wherein said coding region from a plant sucrose synthase gene comprises a nucleotide sequence encoding a polypeptide comprising the amino acid sequence of SEQ ID NO: 2.

4. The method according to any one of claims 1, 2, or 3, wherein said promoter is a subterranean clover stunt virus promoter.

5. A cotton plant comprising in its genome a chimeric DNA comprising the following operably linked DNA fragments:
   a plant expressible promoter selected from a constitutive promoter, a subclover stunt virus promoter, a fiber specific promoter, a primary cell wall promoter or a secondary cell wall promoter;
   the coding region from a sucrose synthase gene; and,
   a transcription termination and polyadenylation signal which functions in said plant;
   said cotton plant having increased fiber length, compared to cotton plants which do not have said chimeric DNA.

6. A cotton plant according to claim 5, wherein said coding region from a plant sucrose synthase gene is translated into an active plant sucrose synthase protein.

7. The cotton plant according to claim 5, wherein said sucrose synthase gene comprises a nucleotide sequence encoding a polypeptide comprising the amino acid sequence of SEQ ID NO: 2.

8. Seeds of a cotton plant according to any one of claims 5, 6, or 7, said seed comprising said chimeric DNA.

9. Fibers with increased fiber length, isolated from cotton plants according to any one of claims 5, 6, or 7.

10. Cotton plants obtained through the methods of any one of claims 1, 2, or 3.

11. Cotton plants obtained through the method of claim 4.

* * * * *